United States Patent
Seelig et al.

(10) Patent No.: US 7,745,594 B2
(45) Date of Patent: Jun. 29, 2010

(54) NUCLEIC ACID-BASED LOGIC CIRCUITS

(75) Inventors: Georg Seelig, Pasadena, CA (US); David Soloveichik, Los Angeles, CA (US); Erik Winfree, Altadena, CA (US); David Zhang, Overland Park, KS (US)

(73) Assignee: California Institute of Technology, Pasadena, CA (US)

( * ) Notice: Subject to any disclaimer, the term of this patent is extended or adjusted under 35 U.S.C. 154(b) by 1011 days.

(21) Appl. No.: 11/490,948

(22) Filed: Jul. 21, 2006

(65) Prior Publication Data

US 2007/0072215 A1   Mar. 29, 2007

Related U.S. Application Data

(60) Provisional application No. 60/701,750, filed on Jul. 21, 2005.

(51) Int. Cl.
*C07H 21/04* (2006.01)
*C07H 21/02* (2006.01)
*C12N 15/11* (2006.01)

(52) U.S. Cl. .................. 536/23.1; 536/24.2; 977/704; 977/711

(58) Field of Classification Search .......... None
See application file for complete search history.

(56) References Cited

U.S. PATENT DOCUMENTS

| 5,561,071 | A  | 10/1996 | Hollenberg et al. |
|---|---|---|---|
| 5,955,322 | A  | 9/1999 | Guarieri et al. |
| 6,706,474 | B1 | 3/2004 | Lu et al. |
| 2004/0070426 | A1 | 4/2004 | Stojanovic |
| 2005/0112614 | A1 | 5/2005 | Cook et al. |
| 2005/0205434 | A1 | 9/2005 | Sen et al. |
| 2006/0051838 | A1 | 3/2006 | Hwa et al. |
| 2006/0281121 | A1 | 12/2006 | Unger et al. |

OTHER PUBLICATIONS

Gardner, Timothy S.; C. Cantor; and J. Collins "Construction of a genetic toggle switch in *Escherichia coli*" Nature, Jan. 20, 2000, vol. 403, pp. 339-342.
Elowitz, Michael B.; and S. Leibler "A synthetic oscillatory network of transcriptional regulators" Nature, Jan. 20, 2000, vol. 403, pp. 335-338.
Benenson, Yaakov; B. Gil; U. Ben-Dor; R. Adar; and E. Shapiro "An autonomous molecular computer for logical control of gene expression" Nature, Apr. 28, 2004; DOI 10,1038.
Yurke, Bernard; and A. Mills, Jr. "Using DNA to Power Nanostructures" Genetic Programming and Evolvable Machines, Feb. 7, 2004, 4,111-122.
Kim, Jongmin; J. Hopfield and E. Winfree "Neural network computation by in vitro transcriptional circuits" Adv. Neural Inf. ( Process (MPS) 17:681-688, 2004.
Issacs, Frarren. J.; D. Dwyer; C. Ding; D. Pervouchine; C. Cantor and J. Collins; "Engineered riboregulators enable post-transcriptional control of gene expression" Nature Biotechnology published online on Jun. 20, 2004, pp. 1-7.
Fitch, Walter M.; "Calculating the expected frequencies of potential secondary structure in nucleic acids as a function of stem length, loop size, base compositions and nearest neighbor frequencies" Nucleic Acids Research, 1983, vol. 11, No. 13, pp. 4655-4663.
Adleman, Leonard M., "Molecular Computation of Solutions to Combinatorial Problems" Nov. 11, 1994, Science, vol. 266, pp. 1021-1024.

*Primary Examiner*—James Martinell
(74) *Attorney, Agent, or Firm*—Joseph R. Baker, Jr.; Gavrilovich Dodd & Lindsey LLP

(57) ABSTRACT

This invention relates to nucleic acid-based logic gates. The invention further relates to circuits comprising nucleic acid-based logic gates and methods of performing operations with the gates and circuits provided herein.

37 Claims, 22 Drawing Sheets
(22 of 22 Drawing Sheet(s) Filed in Color)

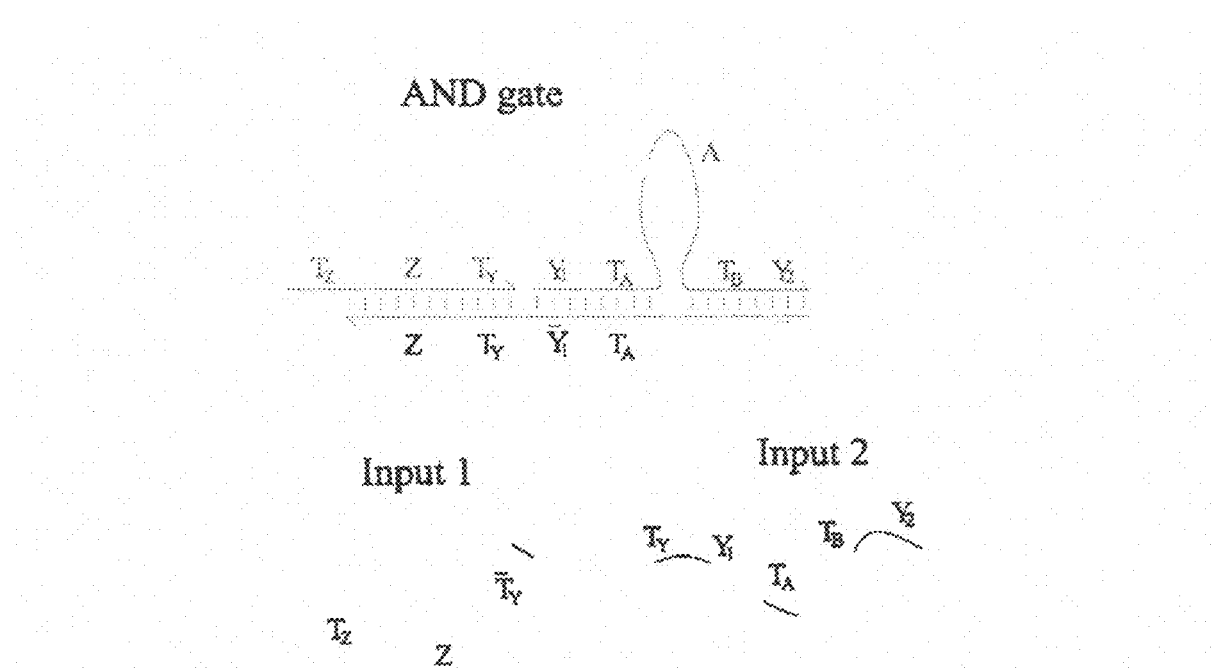
Figure 1 The components of a two-input AND gate
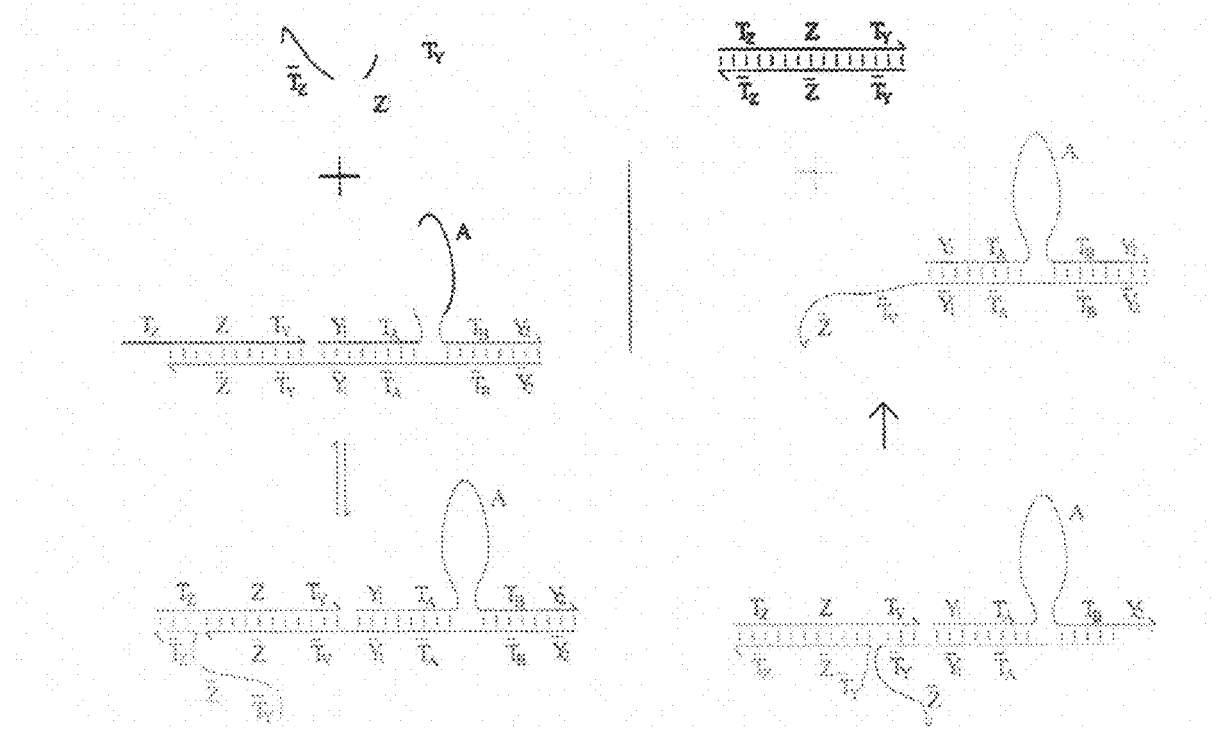
Figure 2: Input 1 binds to the Gate

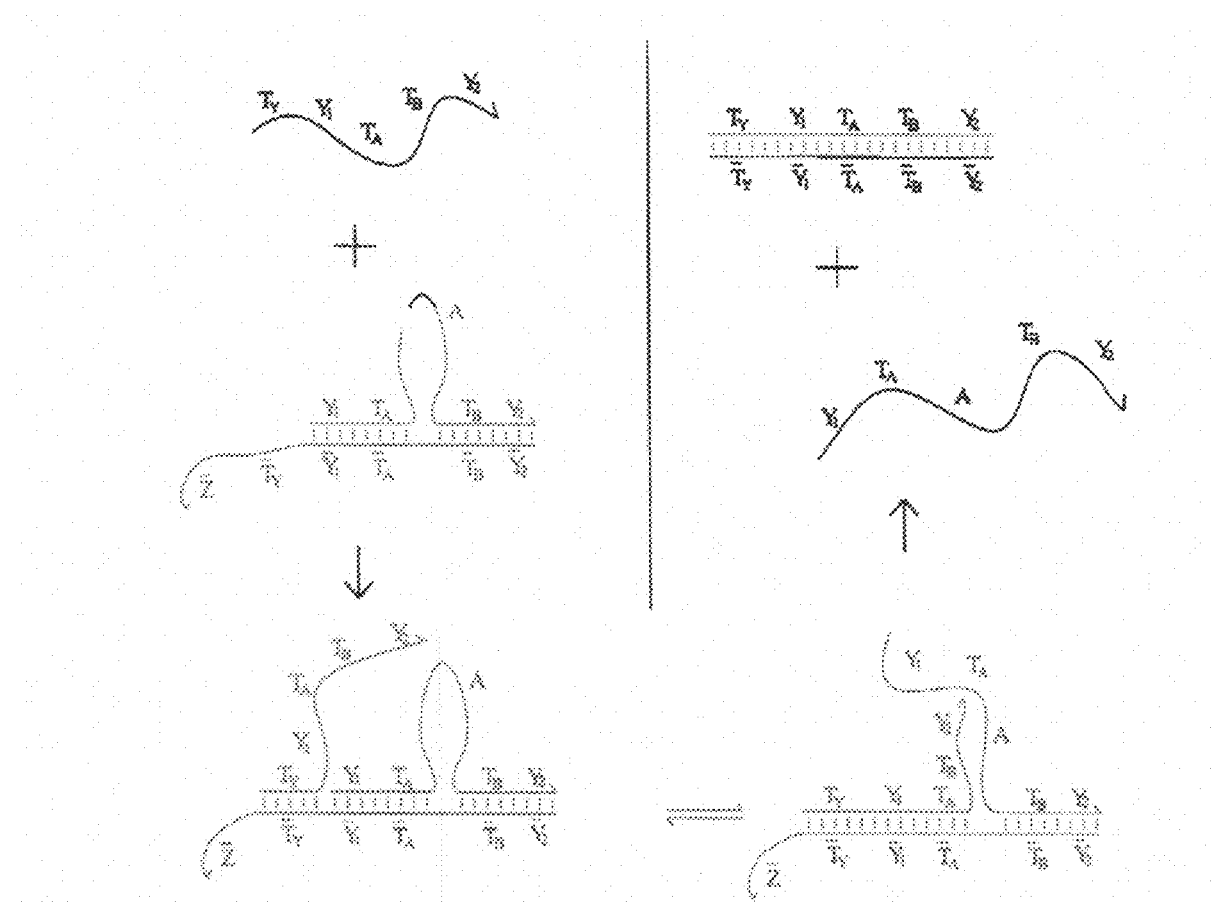
Figure 3: Input 2 binds to the reduced Gate, and liberates output
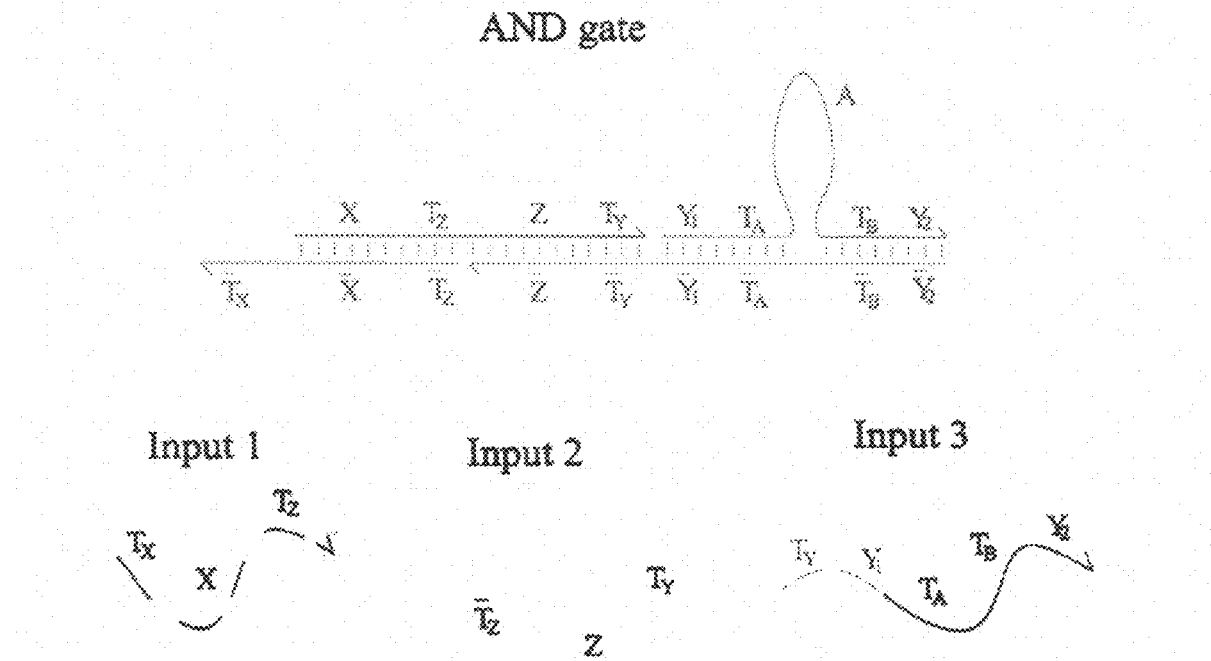
Figure 4: 3 input variation of the single-stranded input gate

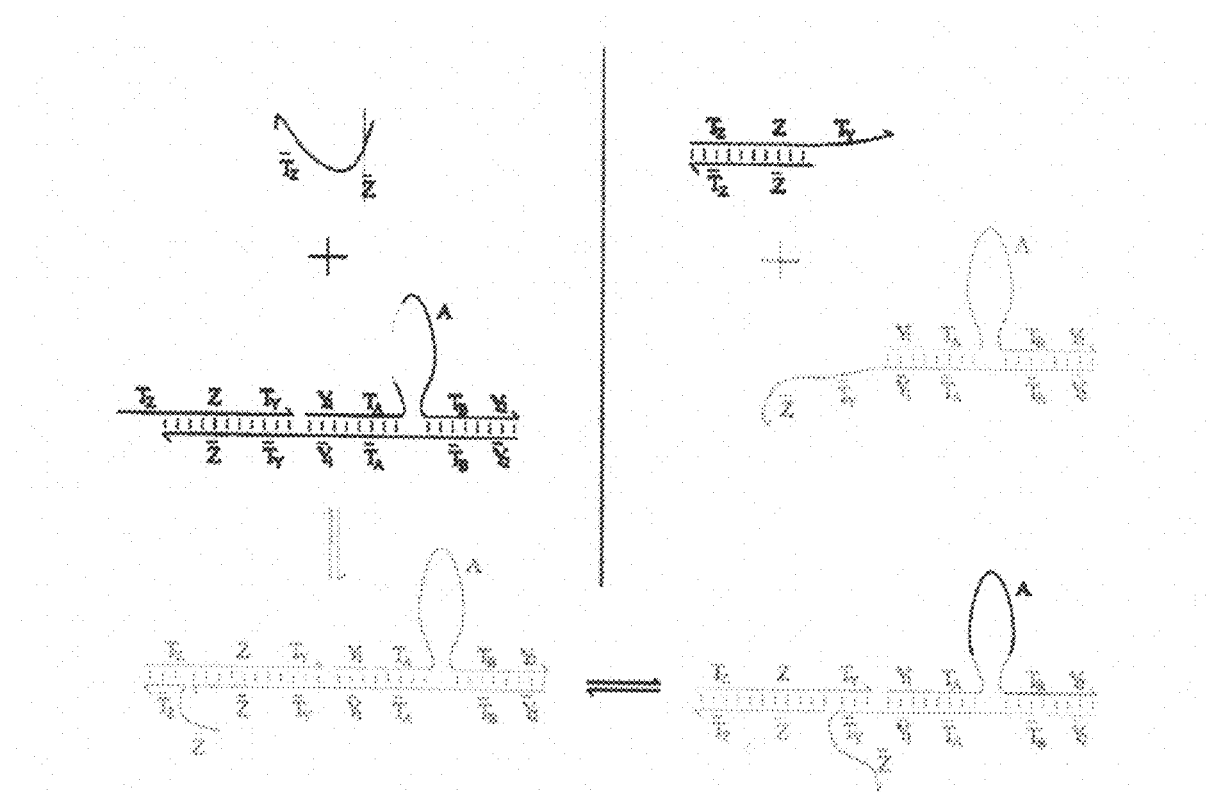
Figure 5: AND Gate with Truncated Inputs
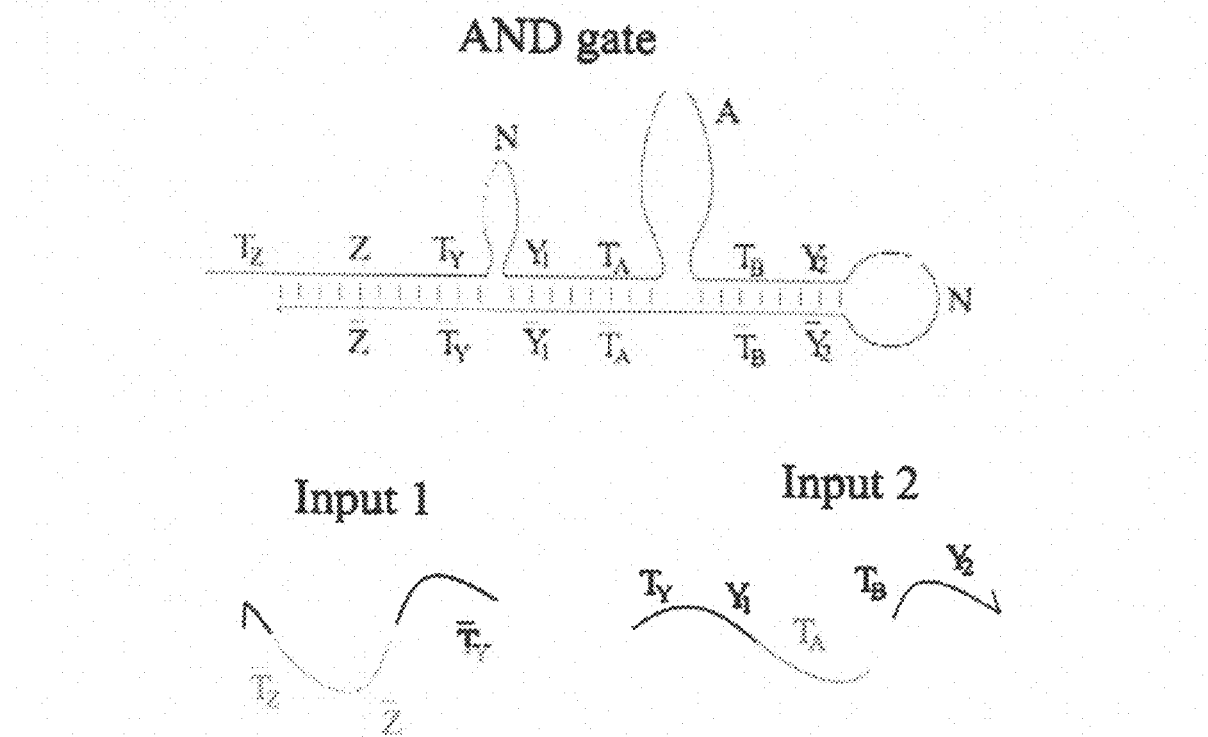
Figure 6: A Non-Dissociative AND Gate

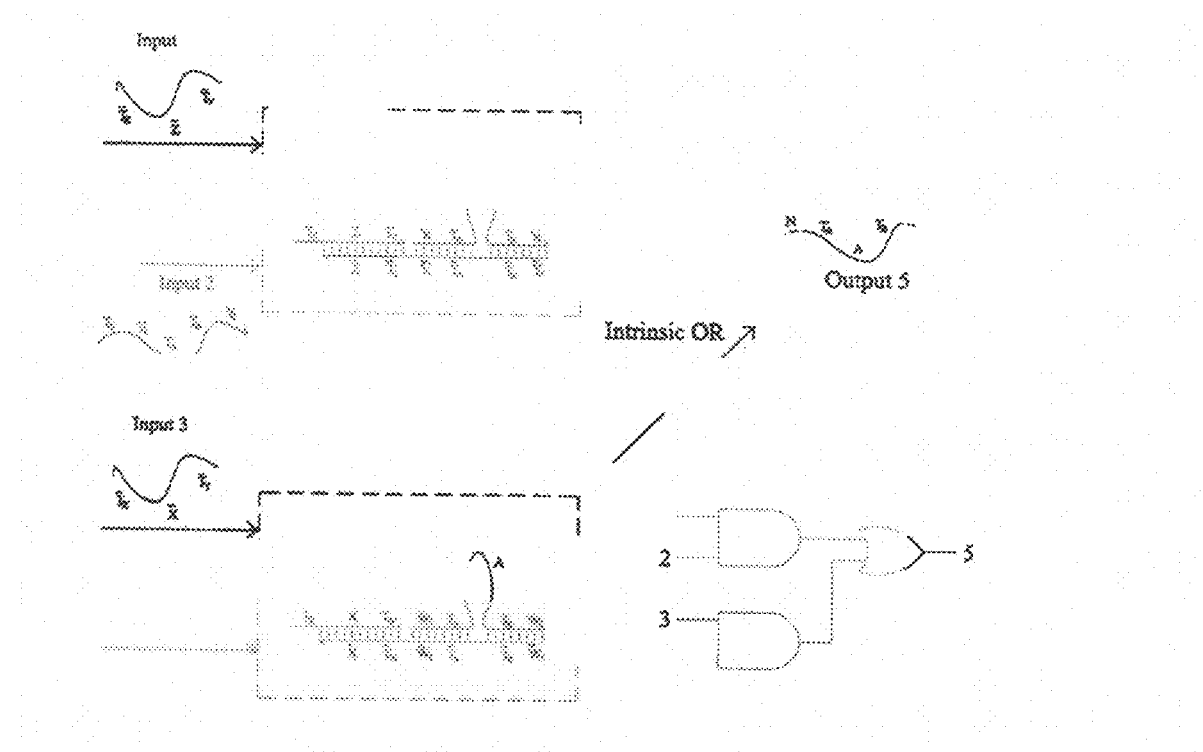
Figure 7: A simple circuit, and its implementation
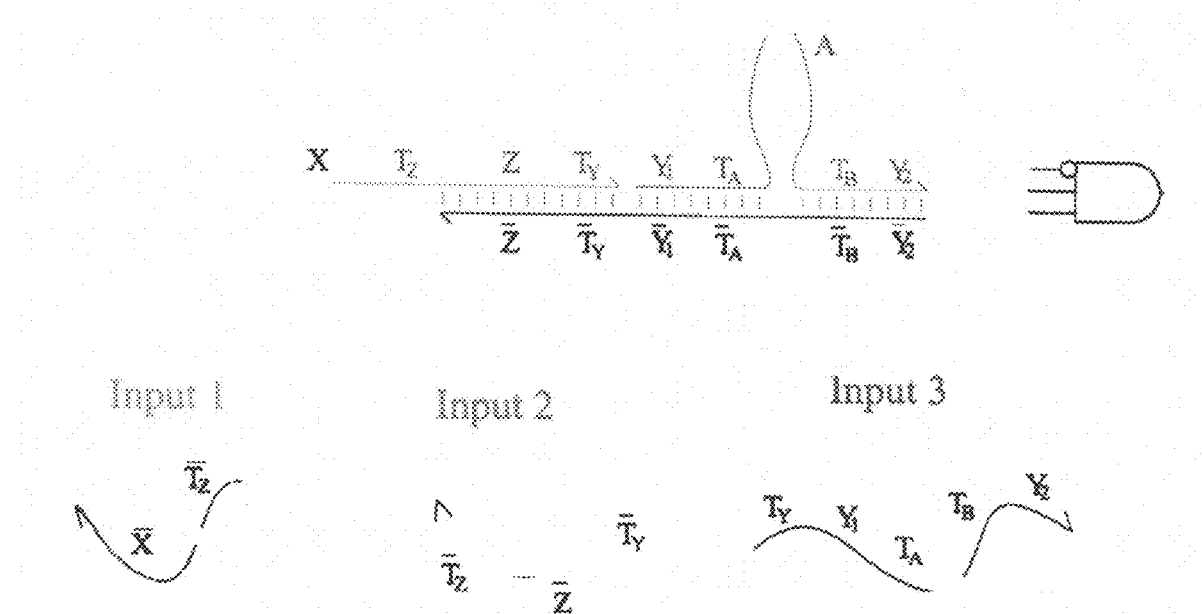
Figure 8: A gate with negated inputs and its circuit representation.

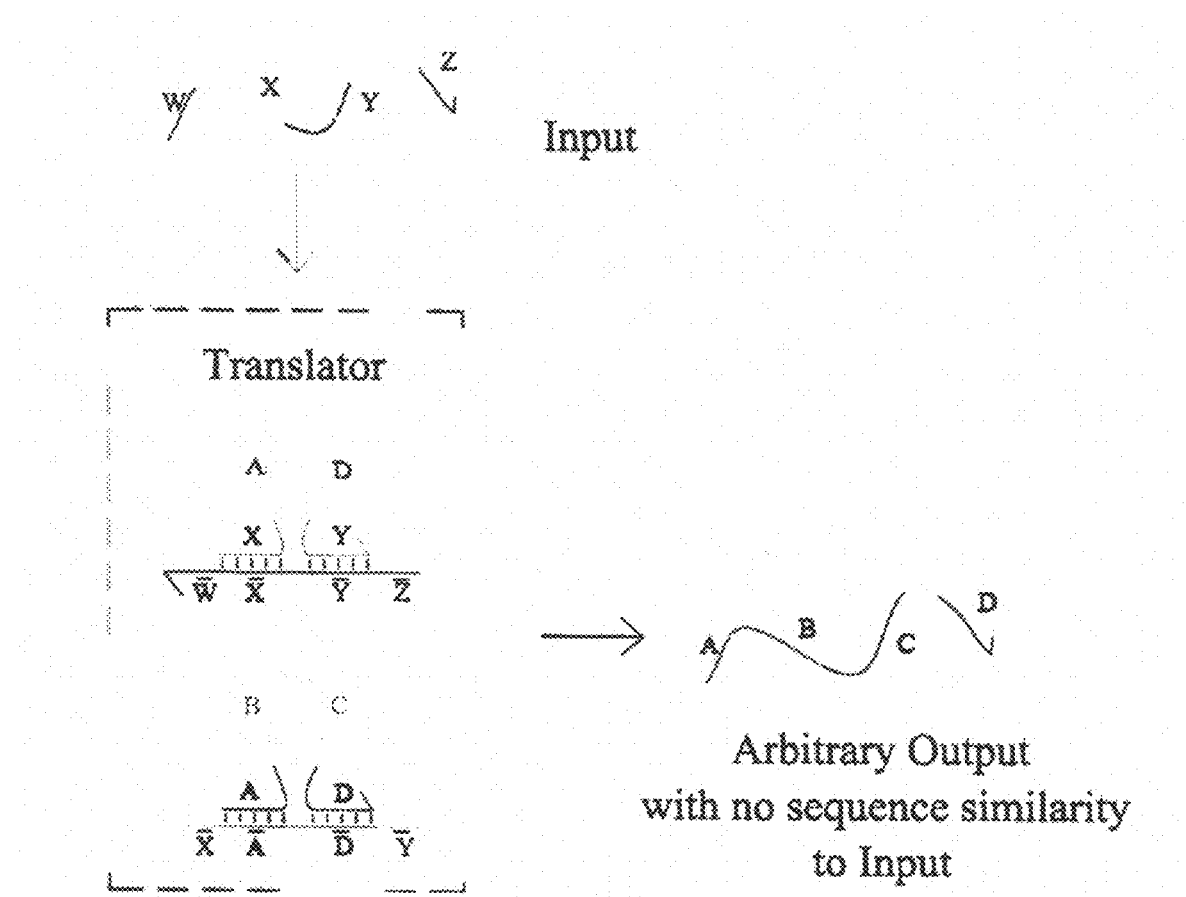
Figure 9: Translation to a different sequence
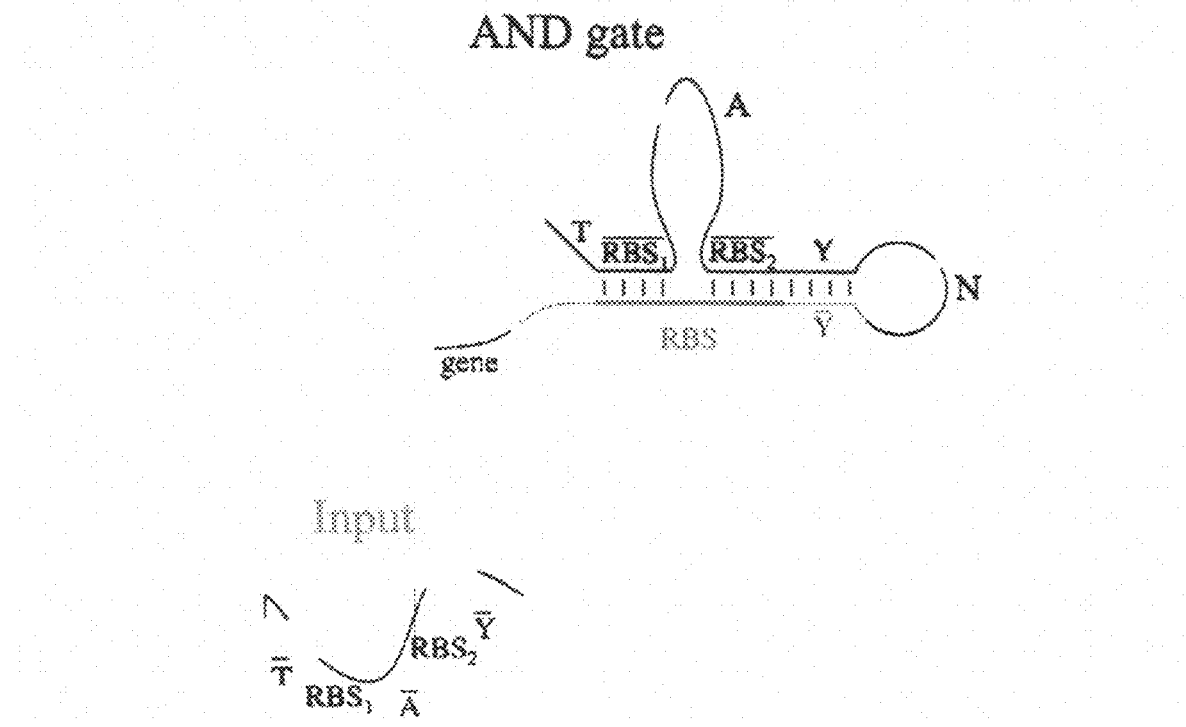
Figure 10: A protein translation control gate.

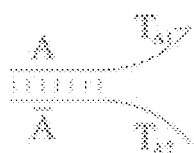
Input A
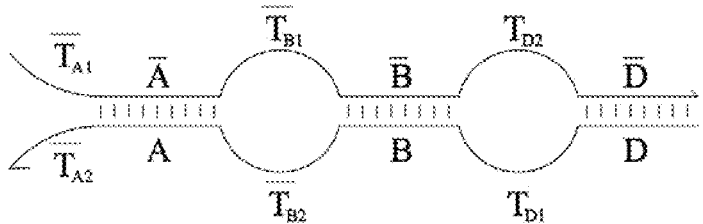
Gate $G_{AB}^{D}$
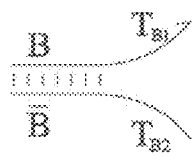
Input B
Figure 11: The components of the double-stranded AND gate
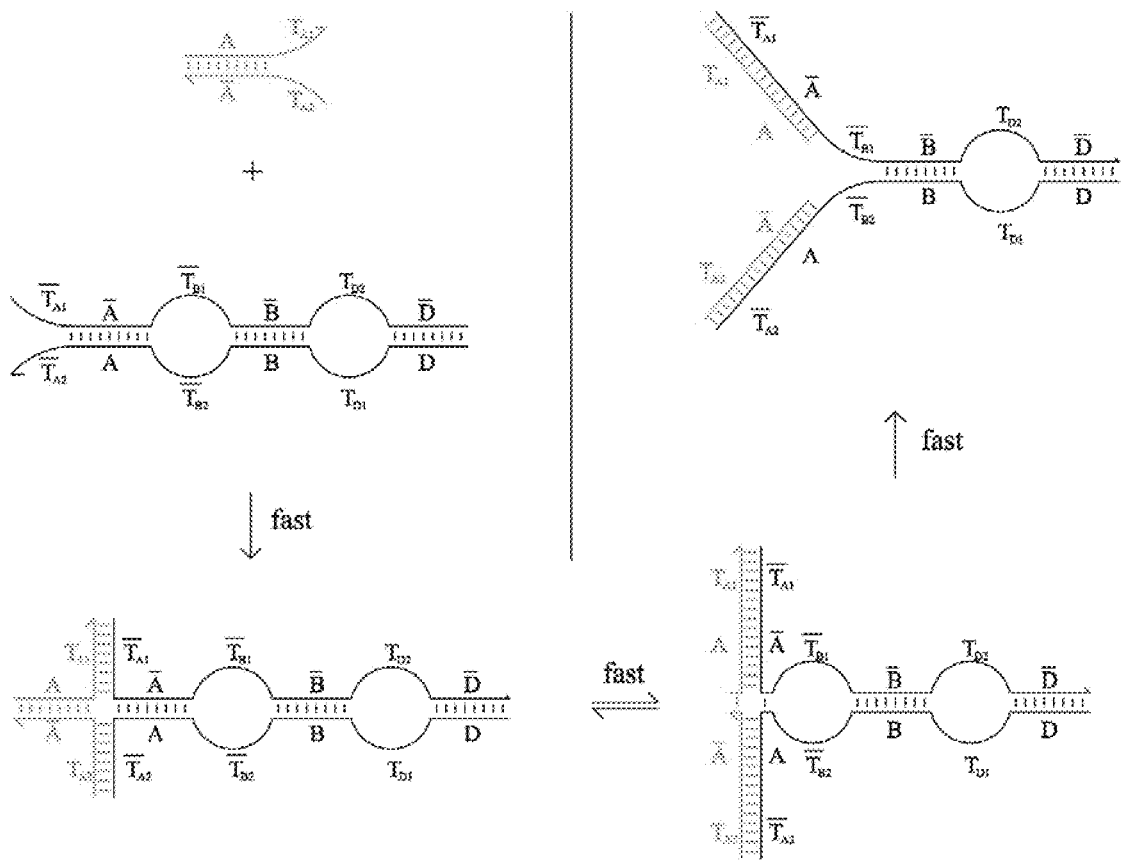
Figure 12: Input A binds to the gate, and opens the binding site for B

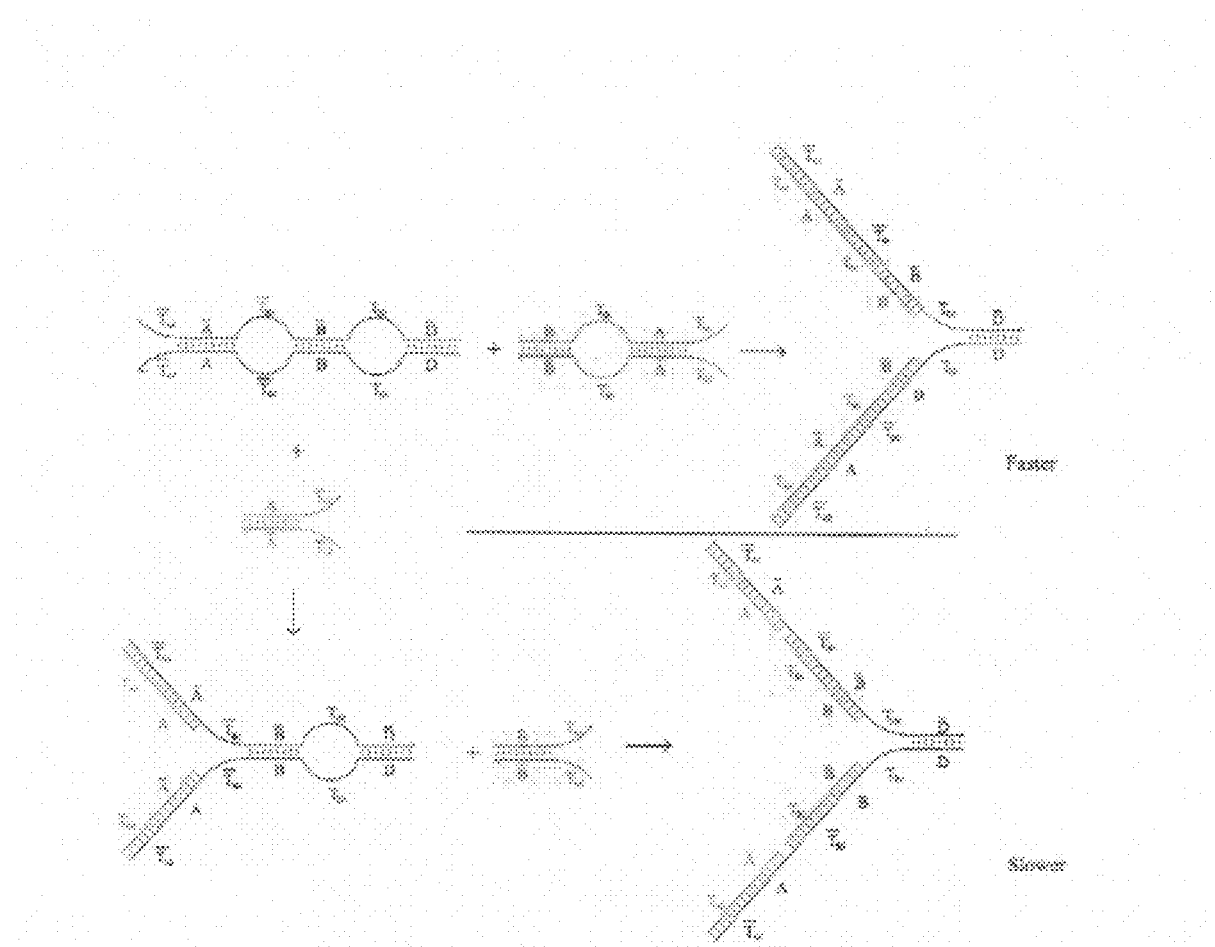
Figure 13: Multi-layered input, before and after binding to a gate

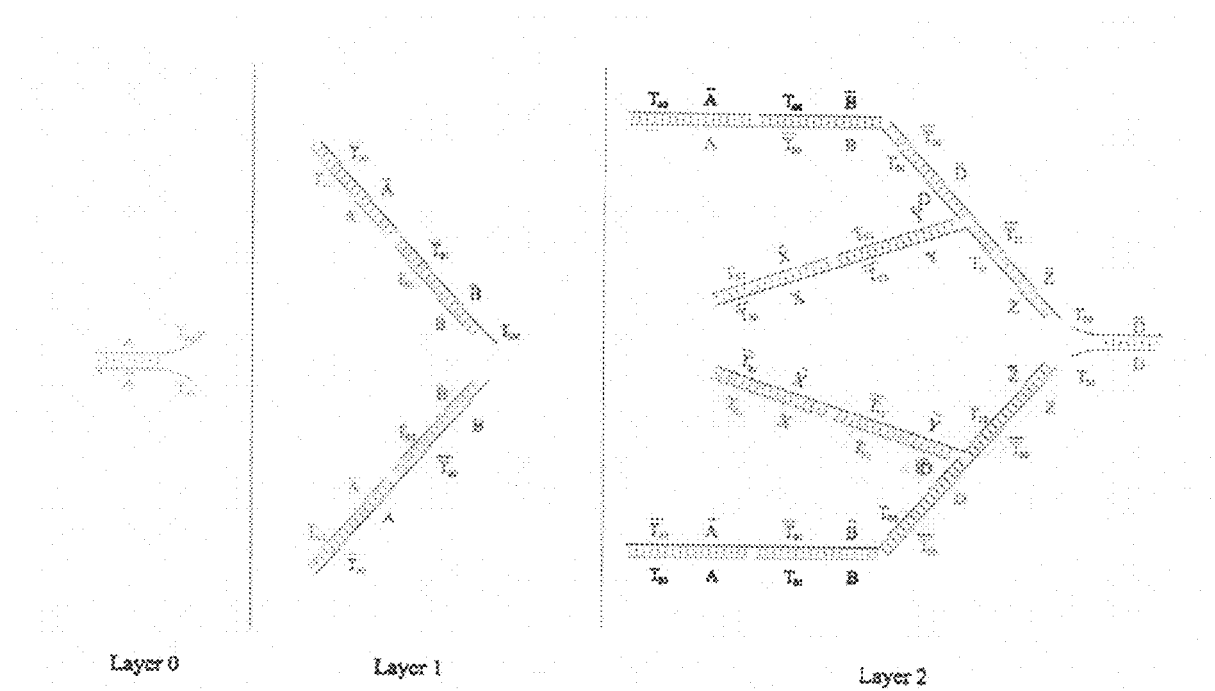
Figure 14: Input aggregation in a 2-layer circuit
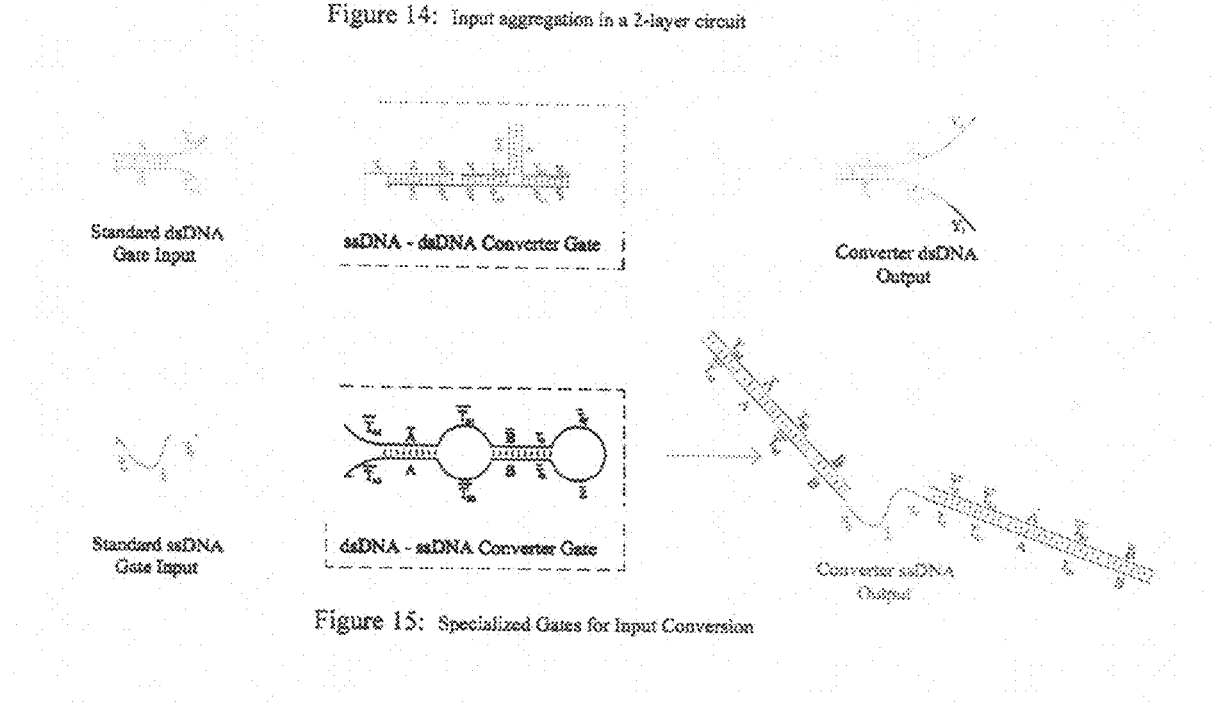
Figure 15: Specialized Gates for Input Conversion

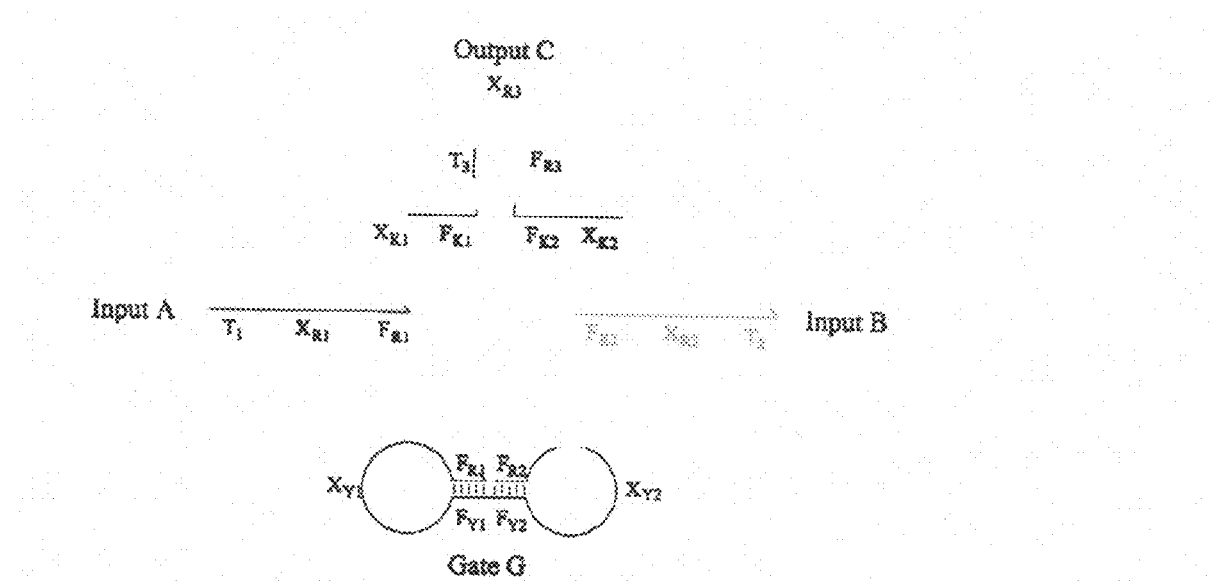
Figure 16: The components of the triplex NAND gate
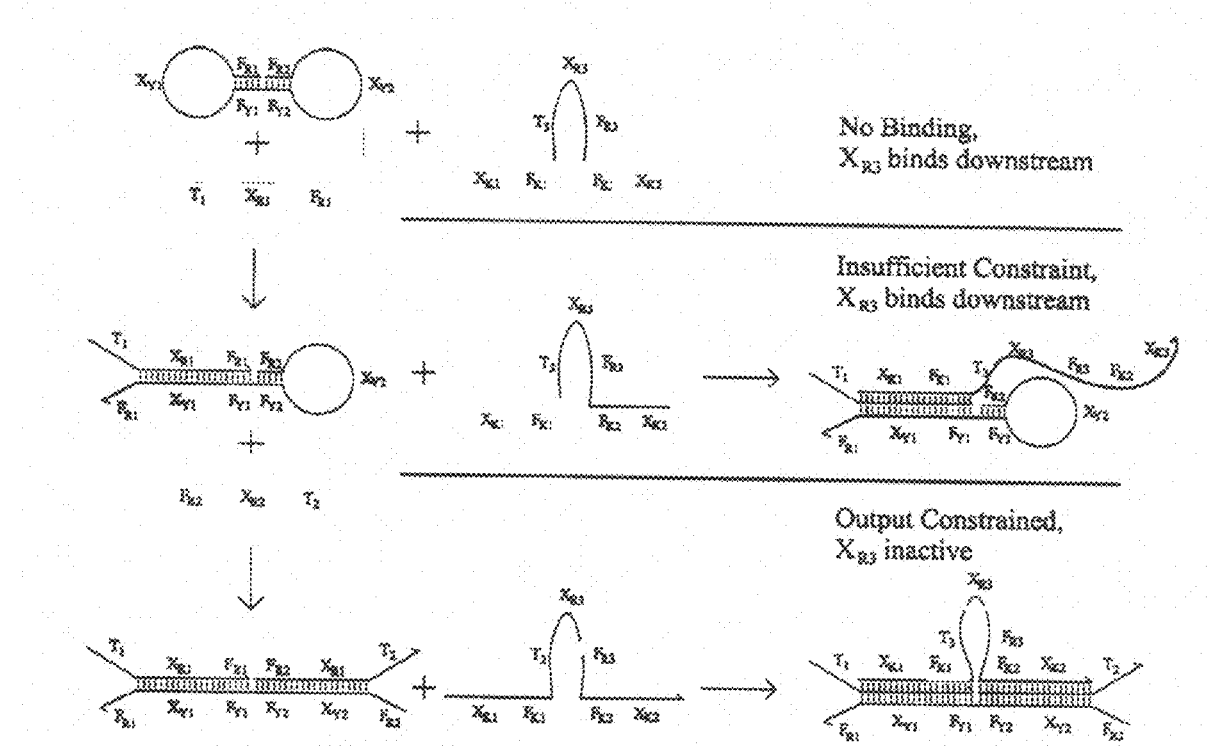
Figure 17: Function of the NAND gate

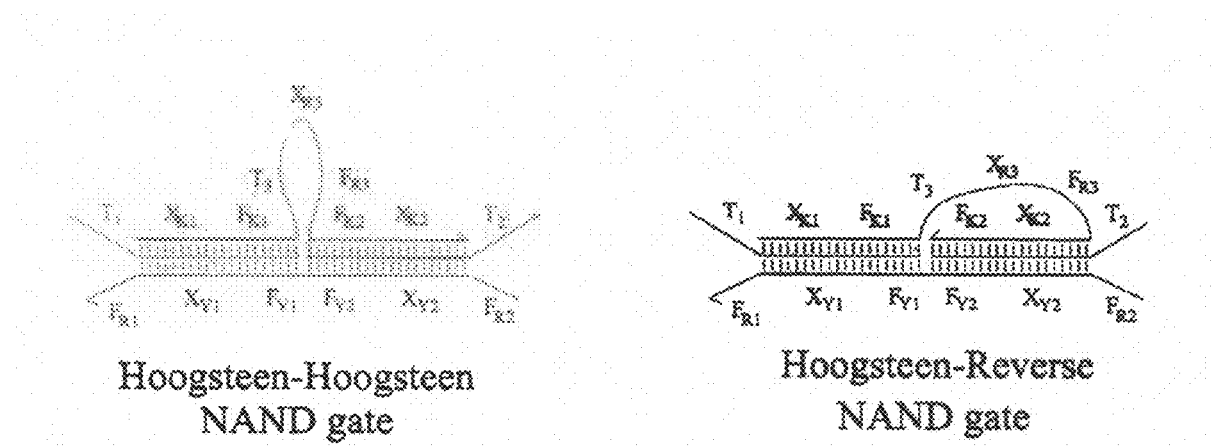
Figure 18: Hoogsteen-Reverse variation

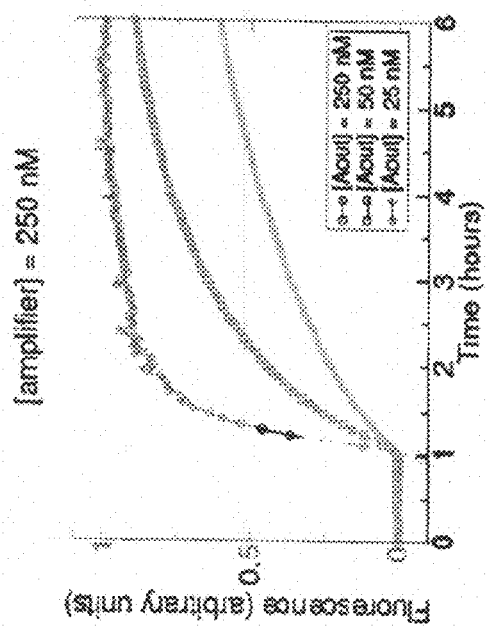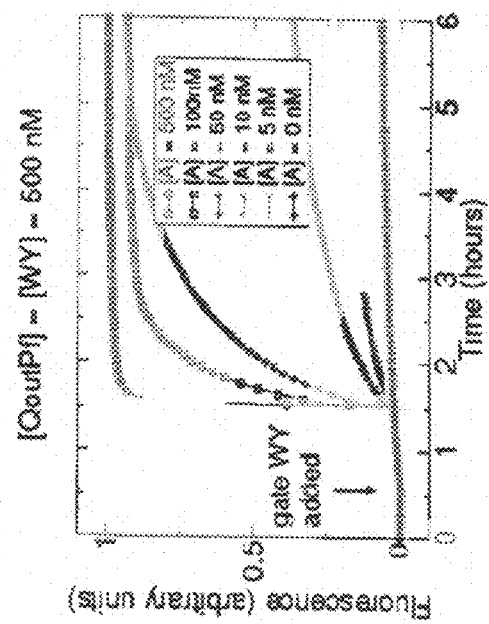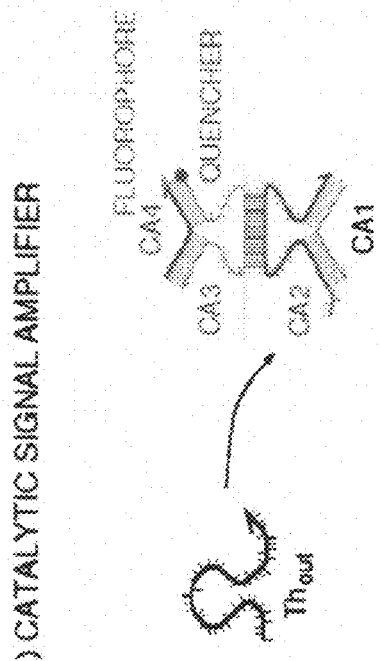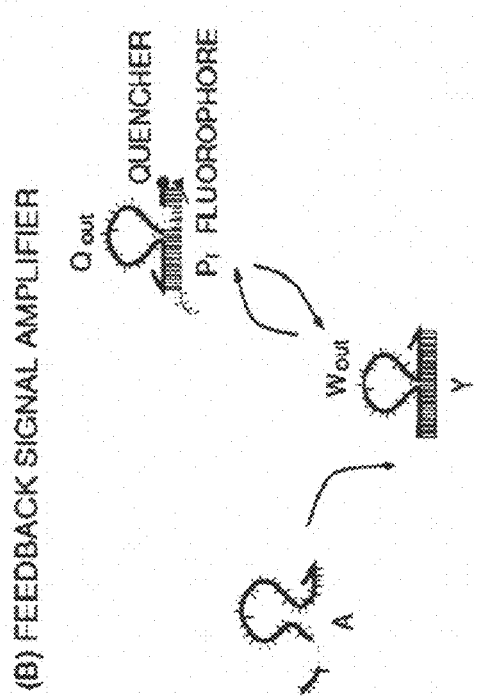
FIGURE 25

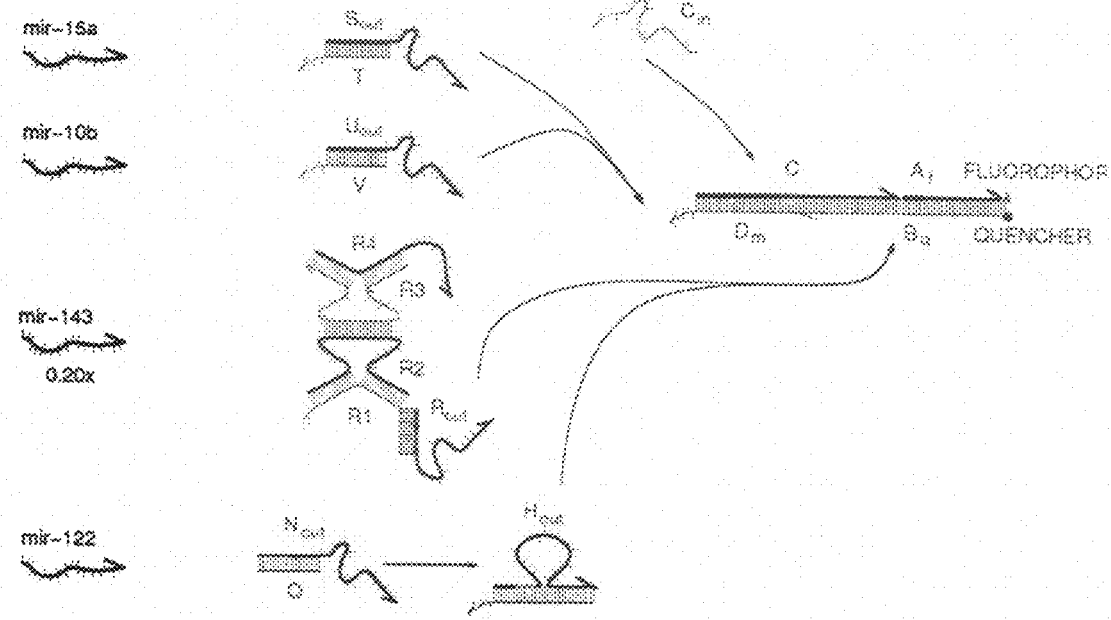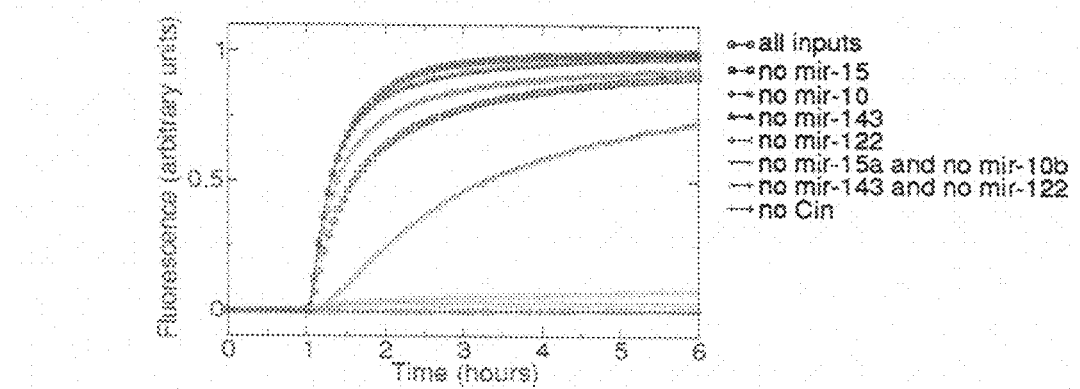
FIGURE 28

NUCLEIC ACID-BASED LOGIC CIRCUITS

CROSS REFERENCE TO RELATED APPLICATIONS

This application claims priority to U.S. Provisional Application Ser. No. 60/701,750 filed Jul. 21, 2005, the disclosure of which is incorporated herein by reference.

STATEMENTS REGARDING FEDERALLY SPONSORED RESEARCH

The invention was funded in part by Grant Nos. 0093846 and 0506468 awarded by the National Science Foundation (NSF). The government may have certain rights in the invention.

TECHNICAL FIELD

This invention relates to nucleic acid-based logic gates. The invention further relates to circuits comprising nucleic acid-based logic gates.

BACKGROUND

Computation with biomolecules provides a basis for manufacturing high-density nano-scale computers. The massive parallel processing potential of such computers makes them ideally suited to solving small-scale NP-complete problems. Further, biomolecular-based computers allow for the embedded control of synthetic control systems and nano-fabrication techniques. Components suitable for use in biomolecular computers are generally compatible with biological environments. Accordingly, biomolecular computers can be used as logic controllers in biological systems generally unsuitable for incorporation of standard silicon-based chips.

SUMMARY

Provided herein are nucleic acid based logic gates, circuits containing a plurality of such gates, and methods of constructing and using such gates. Accordingly, in various embodiments, a nucleic acid based logic gate is provided. The gate includes at least one output oligonucleotide that includes a first region comprising at least one toehold binding domain that forms a duplex with a complementary nucleic acid sequence associated with a gate oligonucleotide. The first region further includes a second region operably associated with the first region and comprising at least one single-stranded domain comprising an oligonucleotide that, upon release, functions as an input nucleotide sequence for a subsequent logic gate or as a signal sequence for detection of an operation, or a combination thereof. The output oligonucleotide further includes a third region operably associated with the second region and comprising a nucleic acid sequence that forms a duplex with a complementary nucleic acid sequence associated with a gate oligonucleotide. The logic gate also includes at least one gate oligonucleotide that include a first region comprising a single-stranded toehold binding domain complementary to an input nucleotide sequence, and a second region comprising a nucleic acid sequence complementary to, and forming a duplex with, the first and third regions of the output nucleotide.

In general, oligonucleotides utilized herein can be comprised of RNA or DNA, or variants thereof. For example, the input oligonucleotide or output oligonucleotide can include a peptide nucleic acid. The length of the oligonucleotides will vary depending upon their use in a particular gate or circuit. Exemplary lengths include 10 to about 200, or about 100, or about 50 nucleotides in length.

In some aspects, the output oligonucleotide can function as an input oligonucleotide to a downstream gate. In other aspects the output oligonucleotide is detectably labeled with, for example, a fluorescent label, a material whose conductivity changes to indicate an output state, or a material whose magnetization changes to indicate the output state.

In other aspects, a gate provided herein can be a logical AND gate, a logical AND NOT gate, a logical NOT gate. In other aspects, the gate is a logical sensor gate.

In some aspects, the input oligonucleotide is an oligonucleotide associated with a disease marker.

In another embodiment, a method of performing a logical operation is provided. The method includes contacting a gate described above with a first input oligonucleotide that forms a duplex with a first toe-hold binding domain associated with a first gate oligonucleotide, wherein the first gate oligonucleotide is partially duplexed with a gate complex. The method further includes displacing the gate oligonucleotide from the gate complex by branch migration, thereby exposing a second toe-hold binding domain associated with a second gate oligonucleotide duplexed with an output oligonucleotide. The method further includes contacting the second toe-hold binding domain with a second input oligonucleotide and displacing the second gate oligonucleotide from the gate complex by branch migration, thereby releasing the output oligonucleotide. Release of the output oligonucleotide indicates that a logical operation has been performed.

In some aspects output oligonucleotide functions as an input nucleotide sequence for a subsequent logical operation or as a signal sequence for detection of an operation, or a combination thereof. Accordingly, the output oligonucleotide can be detectably labeled. In some aspects of a method provided herein, the input oligonucleotide is an oligonucleotide associated with a disease marker and the operation involves detection of a disease marker.

In other aspects, the operation is transduction of an output oligonucleotide to a different gate, such as a logical AND gate, a logical AND NOT gate, a logical NOT gate, a translator gate, a repeater gate or a logical sensor gate.

In some aspects of the method, a translator gate provides an output oligonucleotide to a subcircuit.

In another embodiment, a circuit comprising a plurality of logic gates is provided. A circuit can be a Boolean circuit. The circuit can compute in multi-rail logic format.

According to another aspect of the invention, the logic gate may be arranged and used to detect a disease marker, wherein the disease marker has been translated into an oligonucleotide or a polypeptide. The logic gate may be arranged and used to signal a disease marker, wherein the disease marker has been translated into an oligonucleotide.

According to another aspect of the invention, a plurality of logic gates of the type described above is provided, wherein the output of one gate is arranged as the input of another gate. The product of one gate may be arranged to be the input of another gate.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 depicts components of a two-input AND gate.

FIG. 2 depicts binding of a first input to an AND gate.

FIG. 3 depicts binding of a second input gate to an AND gate.

FIG. 4 depicts alternative binding of a single-stranded gate.

FIG. 5 depicts an AND gate with truncated inputs.

FIG. 6 depicts a non-dissociative AND gate.

FIG. 7 depicts a circuit and its implementation.

FIG. 8 depicts a gate with negated inputs and its circuit representation.

FIG. 9 depicts translation to a different sequence.

FIG. 10 depicts a protein translation gate.

FIG. 11 depicts components of a double-stranded AND gate.

FIG. 12 depicts a first input A binding to a gate and opening a binding site for a second input B.

FIG. 13 depicts a multi-layered input gate before and after binding to a gate.

FIG. 14 depicts input aggregation in a two-layer circuit.

FIG. 15 depicts exemplary specialized gates for input conversion.

FIG. 16 depicts components of the triplex NAND gate.

FIG. 17 depicts an exemplary function of a NAND gate.

FIG. 18 depicts a Hoogsteen-reverse variation for a NAND gate.

FIG. 22, panel B depicts an exemplary translator design.

FIG. 25, panel A depicts a catalytic signal amplifier.

FIG. 25, panel B depicts a feedback signal amplifier.

FIG. 28, panels A and B, depict an exemplary circuit with an input amplifier.

Like reference symbols in the various drawings indicate like elements.

DETAILED DESCRIPTION

Figure 19:
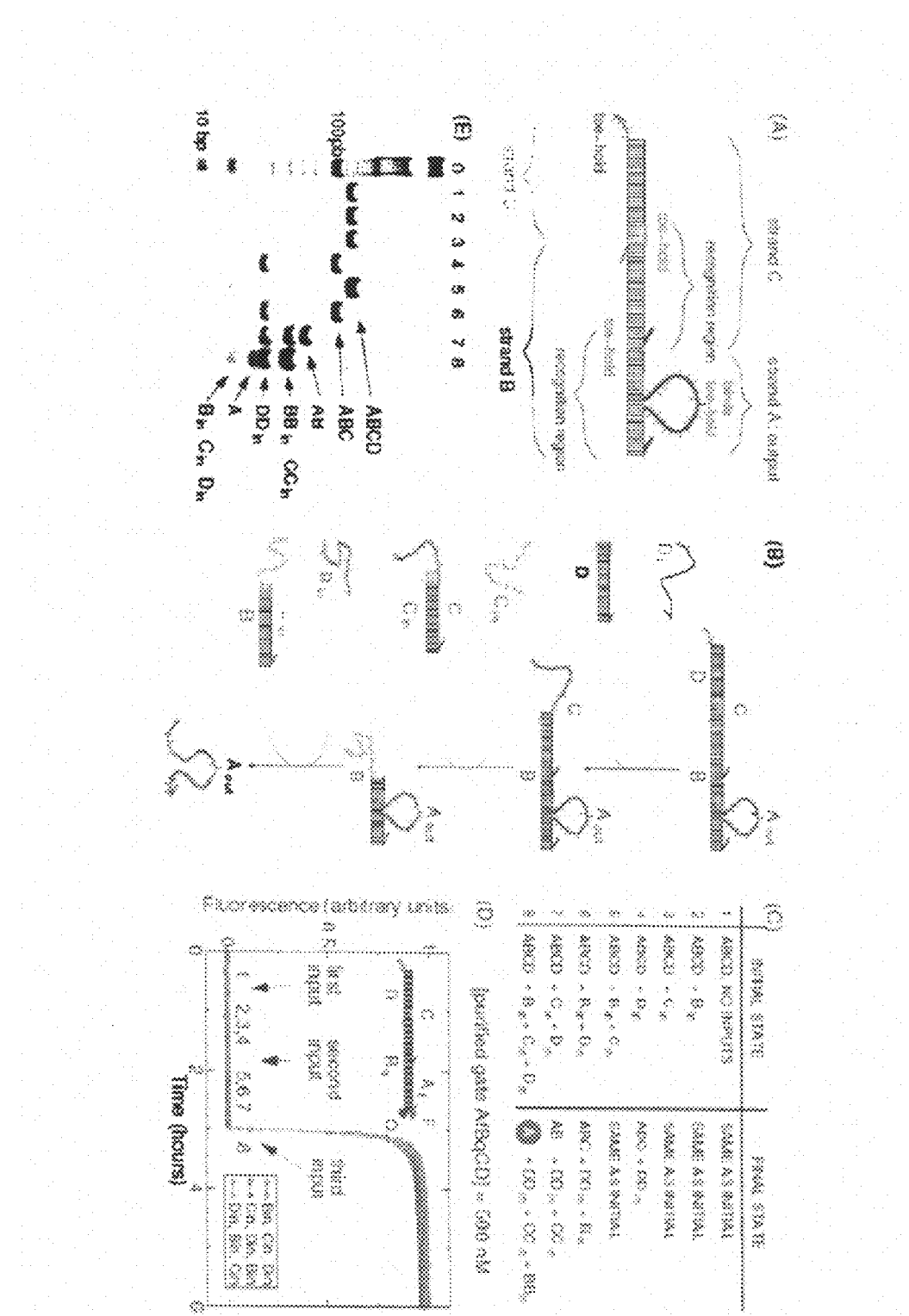
FIG. 19, panels A-D, depict a schematic of exemplary gate operation.

Before describing the invention in detail, it is to be understood that the inventions are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the invention pertains. Although any methods and materials similar or equivalent to those described herein can be used in the practice for testing of the invention(s), specific examples of appropriate materials and methods are described herein.

Watson-Crick interactions are specific and predictable. In addition, the space of available sequences is exponential in the length of the sequence and thus it is possible to find sequences that interact comparatively weakly with a given, pre-defined set, thus minimizing cross-talk. These properties render nucleic acids a promising material for the construction of chemical logic gates and circuits, both in vitro and in vivo. Whereas allosteric ribozymes that take small molecules as input have been shown to perform logical functions, their output (a cleaved or ligated oligonucleotide) is of a different form as the input, and hence cascading is difficult. Initial in vitro work to create deoxyribozymes controlled by input oligonucleotides allowed the construction of complex automata performing multiple logical operations in parallel. Deoxyribozyme-based logic has been extended to create a single-step signaling cascade and a feedback cycle that acts as an exponential chain reaction. An alternative approach to nucleic-acid based automata combines sequence recognition for logical control with enzyme activity to make or break covalent bonds. Nucleic acid reactions can be driven without the need for enzyme or (deoxy)ribozyme catalysis, and this principle has been exploited to construct DNA-based logic gates and signaling cascades.

Provided herein are nucleic acid-based logic gates using single stranded nucleic acids as inputs and outputs. The gates can be included in a multilayered logic circuit that allows the implementation of universal Boolean logic. Exemplary AND, OR, and NOT gates, signal restoration, cascading, amplication, and feedback are demonstrated in the examples set forth below. The gates rely exclusively on hybridization reactions (e.g., sequence recognition and strand displacement) without making or breaking covalent bonds, and therefore can operate in the absence of enzyme or (deoxy)ribozyme catalysis. Nucleic acids like micro RNAs can serve as inputs, and the gates work reliably in a background of nucleic acids as discussed below. Such biocompatible gates and circuits may have applications to the analysis of complex biological samples, such as detection of micro RNA expression patterns, or ultimately to the control of cellular function in vivo.

Digital electronic circuits use Boolean logic with the values "0" and "1" usually represented as low and high voltage values. A small set of logic gates (e.g. AND, OR, and NOT) are sufficient for computing arbitrary Boolean functions. In a digital chemical circuit, bits of information can be encoded as concentrations of signaling molecules processed by molecular logic gates. Based on the current understanding of the design of digital electronic circuits, a list of desired circuit properties can be compiled. First, to cascade a signal, inputs and outputs to all circuit components should be of the same form. Second, a buffering mechanism should be available to compensate for signal loss and leakage. Signal restoration through thresholding and amplification (gain) is particularly important in multi-layered circuits where small errors may be compounded as they propagate through the circuit. Third, for plug-and-play circuit construction, circuit components should also be well isolated and modular. Isolation demands that there is no input or output load, i.e. fan-in or fan-out should not lead to loss or gain of signal. In addition, interactions between circuit elements should be specific, there should be no crosstalk and it should be possible to add new components without disturbing the existing circuit. In silicon-based electronic circuits, spatial arrangement and direct wiring can be used to achieve specificity and modularity; in liquid phase chemical circuits, wiring of logic operations needs to be based on specificity of chemical interactions.

Nucleic acids are useful for the construction of chemical logic gates and circuits, both in vitro and in vivo. Specificity of interactions and reliability of molecular design are made possible by the predictability of Watson-Crick base pairing. In addition, the space of available sequences is exponential in the length of the sequence and thus it is generally possible to find sequences that interact comparatively weakly with a given, pre-defined set, thus minimizing crosstalk. Whereas allosteric ribozymes that take small molecules as input have been shown to perform logical functions, their output (a cleaved or ligated oligonucleotide) is of a different form as the input, and hence cascading is difficult. Initial in vitro work to create deoxyribozymes controlled by input oligonucleotides allowed the construction of complex automata performing multiple logical operations in parallel. Deoxyribozyme-based logic has been extended to create a single-step signaling cascade and a feedback cycle that acts as an exponential chain reaction. Recently, engineered nucleic-acid logic switches based on hybridization and conformational changes have already been successfully demonstrated in vivo (Yurke, et al., BioSystems 52:165-174; Yurke et al., Nature 406:605-608). A remaining challenge is to design chemical logic gates such that they can be combined to make large, reliable circuits via the desired digital logic principles discussed herein.

Provided herein are in vitro nucleic acid based logic gates and circuits, and methods of making and using them. A complete set of Boolean logic gates: AND, OR, and NOT were devised using short oligonucleotides as input and output. Because the input and output are of the same form, the gates can be cascaded into multiple layers. The sequences of input and output domains can be chosen with few constraints, which allow the design of circuits with almost no discernible crosstalk and the easy addition of new circuit components. Modularity (plug-and-play) is also achieved by translator gates that can interconvert signals represented by entirely different oligonucleotides, including naturally occurring nucleic acid sequences (micro RNAs). Signal restoration is achieved by threshold and amplifier gates. Amplifier gates can also be used to prevent signal loss with output load.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

As will be described in more detail below, the invention is based, at least in part, on the design of nucleic acid based logic gates such that they can be combined to make large, reliable circuits via desired digital logic principles.

Exemplary applications of enzyme-free biomolecular logic and computation includes in vivo detection of disease. Disease markers such as mRNA, microRNA, and ssDNA (in the case of certain viruses) can form the inputs to the logic circuits implemented by the complexes and methods described herein. The output of the biomolecular logic may be the translation of an output protein, production of microRNAs or activation of an anti-sense RNA. The output may serve to offset the biochemical imbalance caused by the disease in a controlled manner, modulate the activity of the affected cells, or signal the presence of disease in a manner that can be detected by external scans. In addition, the logic gate complexes provided herein can be used for localizing gene expression in tissue sections. For example, an AND gate as provided in the present disclosure can be used to label according to a complex set of conditions (arbitrary Boolean logic expressions) without requiring processing multiple tissue slices.

Further, since the present gates use branch migration rather than hybridization to ensure sequence specificity, they are more sequence specific than current in situ techniques. Indeed, four way branch migration is known to be sensitive to single base changes. Because of the universality of mRNA and its involvement in almost every facet of cellular activity, it is possible that the method of enzyme-free biomolecular computation may be extended to detect and possibly remediate a wide variety of conditions.

In order to effect enzyme-free logic, the complexes and methods provided herein make use of the specific binding of nucleic acid bases to their complements. The simultaneous presence of complementary single-stranded domains in solution provide the system with chemical potential which can be used to perform computation. The process of computation includes the system settling to a lower chemical potential, with fewer bases unbound to their complement, via the process of three way branch migration. While the examples provided below generally discuss the use of gates and inputs made out of DNA, it is understood that any type of nucleic acid can be used. For example, gates and/or inputs can be RNA, PNA, or any other DNA analog that exhibits specific binding. Inputs and gate can be made out of different nucleic acids (e.g. RNA input and DNA gate).

Input and output signals are generally one or more strands with single-stranded domains. The concentrations of exemplary DNA molecules are abstracted to be the analog signal that is to be processed. As in digital or binary logic, high concentration is used to denote high signal ("1"), while low concentration denotes low signal ("0").

As used herein, the term "toehold(s)" includes domains that serve to increase reaction rates by increasing the effective concentrations of relevant strands by co-localization. Toeholds are generally on either the 5' or the 3' end of its strand, so as to maximize flexibility by minimizing geometric and steric constraints. The toehold domains can be short enough to facilitate transitory duplex formation with a complementary sequence, but long enough to increase reaction rates.

Toeholds also serve a fundamental computational function in the present gates and circuits. The output nucleic acid molecules can include single-stranded domains in order to function as downstream inputs to another layer of logic. In addition, the output nucleic acid is protected from immediate reaction. The gate complexes provided herein are designed such that the toehold domains of the output strands are double stranded in the inactive gate, and are thus inactive. Once a gate is provided with the correct set of activating inputs, the output nucleic acid molecule becomes single stranded, thereby detaching from the gate. In the process, the toehold domain becomes single stranded as well, allowing the downstream reaction to proceed.

In various embodiments provided herein, an output oligonucleotide of a gate may comprise a fluorescent readout, electromagnetic readout, colorimetric readout, radiation readout, a light emission readout, and/or an ultraviolet spectral change readout. The output of the gate may comprise a material whose conductivity changes to indicate the output states. The output of the gate may comprise a material whose magnetization changes to indicate the output state.

The logic gate may comprise peptide nucleic acid. The logic gate may comprise DNA. The logic gate may comprise RNA. The DNA may comprise natural DNA. The DNA may comprise synthetic DNA. The RNA may comprise natural RNA. The RNA may comprise synthetic RNA. The logic gate may comprise both natural and synthetic nucleotides.

At least one input may comprise an oligonucleotide. The logic gate may further comprise at least one input based on hybridization. The logic gate may further comprise at least one input based on complementary base pair formation. At least one output may comprise an oligonucleotide.

The number of inputs may be at least two. The gate may be a logical AND gate, comprising at least two inputs, and being in a logical on state only if all inputs are in the same one of two states. The gate may be a logical AND NOT gate, comprising two inputs, and being in a logical on state if and only if one input is in a certain one of two states.

The logic gate may have one input, and form a logical NOT gate, being in a logical on state if the input is in a certain one of two states. The logic gate may comprise more than two inputs, wherein the gate is in a logical on state. The gate may be a logical sensor gate, wherein an input is transduced into an output. The gate may be a logical NOT gate.

According to another aspect of the invention, the logic gate may be arranged and used to detect a disease marker, wherein the disease marker has been translated into an oligonucleotide. The logic gate may be arranged and used to signal a disease marker, wherein the disease marker has been translated into an oligonucleotide. According to another aspect of the invention, a plurality of logic gates of the type described below is provided, wherein the output of one gate is arranged as the input of another gate. The product of one gate may be arranged to be the input of another gate. A plurality of gates may have a common substrate. The substrate of one gate may be the input of another gate.

The gates may operate in implicit OR fashion and form a logical OR gate. The gates may operate in implicit OR fashion and form a logical EXCLUSIVE OR gate. The gates may operate in implicit OR fashion and form a logical NAND gate. A plurality of logic gates may be arranged as a half adder. A plurality of logic gates may be arranged as a full adder.

The logic gate may comprise peptide nucleic acid. The logic gate may comprise DNA. The logic gate may comprise RNA. The DNA may comprise natural DNA. The DNA may comprise synthetic DNA. The RNA may comprise natural RNA. The RNA may comprise synthetic RNA. The logic gate may comprise both natural and synthetic nucleotides.

The logic gate may further comprise a second logic gate, said second logic gate receiving as an input the output of the first logic gate.

Referring now to FIG. 1, the components of a model 2-input AND logic gate are provided. The gate itself is a three-strand complex, and contains the output strand $Y_1 T_A A T_B Y_2$ with sequestered toeholds $T_A$ and $T_B$. The input 1 strand binds first to the AND gate via the exposed single-stranded toehold $T_Z$. Three-way branch migration then occurs, until the $T_Y Z T_Z$ strand is displaced, as shown in FIG. 2, leaving an inert duplex and a truncated AND gate with the $T_Y$ toehold exposed.

Then, input 2 similarly binds to the now-exposed $T_Y$ domain of the reduced AND gate, and displaces the output strand by binding to the $\overline{Y_2 T_B T_A Y_1 T_Y Z}$ strand. Upon completing branch migration, the output strand is released (see FIG. 3) in single-stranded form to effect downstream logic: since the toeholds $T_A$ and $T_B$ are no longer sequestered, the released output strand can act as an input strand for other gates, with toehold $T_A$ or $T_B$ depending on whether it acts as the first or second input. The binding domains (such as Z and $Y_1$) should be long to minimize the rate of spontaneous dissociation, fifteen nucleotides or longer. Extremely long binding domains may cause loop-kissing interactions, or other types of crosstalk.

The presence of input 2 in the absence of input 1 will not cause the output to be released, since all domains on the gate complex complementary to any of input 2 are fully duplex. Specifically, the $T_Y$ toehold which is freed by the addition of input 1 is sequestered. Neither input 1 nor input 2 alone will release the output; thus the DNA complex describe exhibits AND gate behavior.

The design of the gate presented can be extended to arbitrary number of inputs, by increasing the number of strands that compose the gate complex. Further inputs are composed of one binding domain flanked by two toehold domains, just as Input 1 and 2. For example, an extension of the design to 3 inputs is shown in FIG. 4. The logical equivalent of an n-input AND gate requires the use of (n−1) 2-input AND gates. Thus, this variation may reduce circuit complexity, allowing for practical implementation of large circuit designs.

The second toehold domain on all the input strands except those acting as a last input can be removed to allow for reversible reactions (see FIG. 5). After branch migration, the partial duplex is tentatively held by six base pairs, which is weak enough to spontaneously dissociate. However, because this toehold still exists, it is possible for the partial duplex to rebind and for the input to be re-released, and thus equilibrium is established.

Reversible reactions are desirable for input conservation. Because the signal value physically corresponds to concentrations of certain oligonucleotides, depletion due to partial reactions is undesirable. For example, if only the first input of the AND gate is present, it is not desirable for the input to be consumed completely by the AND gates. Thus, reversibility is expected to reduce the need for amplification stages in circuits. Note that if all inputs to the AND gates are present, the release of the output strand is irreversible.

Another implementation of reversible reactions is the non-dissociative version AND gate. Rather than using multiple short oligonucleotides to construct the AND gate, one long oligonucleotide is used instead. Its sequence is the concatenation of all component strands of the original gate, with non-binding domains forming bulges to connect domains which were originally on different oligonucleotides (see FIG. 6). These bulges may not be necessary, but may allow degrees of freedom preventing steric interference.

After the inputs bind to their respective targets and form duplexes, they are still localized within the vicinity of the gate. Combined with the truncated inputs from the previous section, such gates should allow highly reversible reactions.

An additional advantage of the non-dissociative AND gate is that correct stochiometry is achieved automatically. For a 3-input AND gate, the required 1:1:1:1 stochiometry is difficult to achieve without tedious purification steps. On the other hand, very long oligonucleotide sequences required for non-dissociative gates are technically difficult to synthesize. Also, the possible dimerization of the non-dissociative AND gate may present technical challenges in gate characterization.

The advantage of non-dissociative gates is that since they are made out of a single nucleic acid strand, it can be transcribed in vivo as RNA, folding in the process. Intramolecular folding in vivo of similar structural elements (hairloops) is well known.

Besides AND gates, other circuit components are needed to be able to implement arbitrary circuits. The following information describes how to create fan-out, OR gates, NOT gates, modular sub-circuits and signal recovery amplifiers. Also provided is a diagram of how the output of such a circuit can interface with biological activity through specific control of protein translation.

A circuit has fan out if the output of one logic gate is used by more than one downstream gate as input. Fan out is naturally created in the exemplary system by making an output of one AND gate be the input to more than one downstream gate. Note, however, that if n downstream gates receive input from a single AND gate, then this potentially requires n times as many copies of the upstream gate to be active in order to activate a given quantity of the downstream gates.

An alternate solution relies on using different parts of the output strand be inputs to different downstream gates. Let the segment A of the output strand be twice as long, and let $T_A$ and the first half of A be the input to one downstream gate and the other half of A and $T_B$ be the input to another downstream gate. This method does not suffer from the concentration reduction problem of simply using the whole output strand as an input to two different downstream gates because a single output strand can activate both downstream gates. Further, it allows the input strand to the two downstream gates to be different.

Intrinsic OR gates are naturally created if more than one AND gate produces the same output (see e.g., FIG. 7).

Referring to the gate shown in FIG. 8, if inputs 2 and 3 are present, the gate will activate as before. However, if input 1 is present, it hybridizes to the gate, blocking the toehold $T_Z$ and preventing input 2 from initiating branch migration. While the competitive nature of this inhibition may allow some leakage, note that the hybridization reaction of Input 1 with the gate is much faster than the branch migration reaction required for Input 2 and thus is kinetically favored. Further, if region X is sufficiently long, this reaction is also energetically favored as more base pairs are formed than in the attachment of input 2. Thus the presence of input 1 should prevent the activation of the gate even in the presence of the other two inputs. Note that this method of negation requires the concentration of input 1 to be greater than or equal to the concentration of input 2.

Thus, the above gate is activated if and only if inputs 2 and 3 are present but input 1 is not. Similar negated inputs can be created for the second input position of the above gate (i.e. strand $T_Y Z$.).

The systems provided herein can be made modular in the sense that a circuit computing a particular function can be used with different inputs and outputs without necessitating the redesign of the gates. This can be done by creating translator gates, which are single input AND gates (see FIG. 9).

Referring to FIG. 9, one translator allows an arbitrary input/output strand to be effectively converted into another input/output strand as long as they share the same toehold sequence. Two translator gates in sequence allow an arbitrary sequence to be converted to another arbitrary sequence, even if their toehold sequences are different.

Since the gates described by this report will not be 100% efficient, and thus "lose" signal with every layer, signal restoration may be necessary.

Referring to FIG. 10, expression of RNA non-dissociative gates is one possible method of implementing the AND gates provided herein in vivo, because a fully functioning gate can be created from a single transcript through intramolecular interactions only. Since mRNA or microRNAs are single stranded species, they can act as input to or output of in vivo gates directly. This section describes an additional output method suitable for in vivo computation, namely controlled translation of protein.

Referring again to FIG. 10, these gates take a single stranded nucleic acid as input and induce translation of the corresponding protein if and only if the input is present. In the inactive form of the gate, the ribosome binding site (RBS) is sequestered in a double stranded region, preventing ribosome binding. The input strand can strip off the sequestering segment and thereby activate translation. Note that the input strand does not have a complete RBS in order to prevent inadvertent titration of ribosomes. Since the input strand needs to have half of the RBS at one point ($RBS_1$) and half at another ($RBS_2$), a translator may be used upstream to remove the sequence restrictions this imposes (see above).

Referring to FIG. 11, a double-stranded input AND gate is provided. This gate design is characterized by the two-stranded nature of inputs, outputs, and the gate complex itself. This method relies on four way branching migration, rather than three way branch migration as in the case of the single stranded input AND gates. The main advantage of this design is that it minimizes the number of single stranded nucleic acid strands in solution, thereby preventing them from unintentionally binding each other through partial sequence complementarity, or other nucleic acids. Provided in FIG. 11 is a typical two-input gate $G_{AB}^D$.

As can be seen in FIG. 11, the inputs are mostly duplex, except for a 5' toehold overhang on one strand, and a 3' toehold overhang on the other. When the input molecule A binds to the gate G, the two toeholds simultaneously bind their respective complements on G (see FIG. 12). This causes the formation of a four-way junction, which then leads to four-way branch migration of the $n_A$ and $\bar{n}_A$ domains. Upon completion, the mismatch bubble composed of the $T_{B1}$ and $T_{B2}$ domains is then exposed as single-stranded overhangs, which is then free to bind input B.

When both A and B inputs have bound to be gate G, the mismatch bubble composed of $T_{D1}$ and $T_{D2}$ is exposed as the single-stranded overhangs of the $D\overline{D}$ duplex. That complex can serve as the input of a similar downstream gate.

Referring to FIG. 13, multi-layered inputs are provided. By adding one or more duplex regions and mismatch bubbles to the input, and in so doing rendering the input very similar to the gate complex, one can allow for certain multi-layered inputs to advance the state of the gate several steps in rapid succession, faster than several different input molecules binding in series. This feature can be used for the implementation of circuitry with different timing patterns.

Referring to FIG. 14, exemplary single-stranded gates are provided. The primary advantage of this gate is that the number of unconstrained single-stranded DNA bases is small. This prevents unintended interaction of the inputs, gates, and other nucleic acid biochemistry happening concurrently. In general, four way branch migration is slower than three way branch migration used in single-stranded gates.

Referring to FIG. 15, an exemplary model of how both single stranded and double stranded gates can be used together via converter gates is provided.

Referring to FIG. 16, an exemplary triplex NAND gate is provided. This gate draws upon forces other than that of the standard Watson-Crick binding. It's known that the double helix characteristic of B-DNA actually retains binding potential for a third strand. The third triplexing strand also exhibits sequence specificity in binding. The inputs are single-stranded, and composed of three domains, including one toe-hold domain. The gate is a single DNA strand, in the shape of a dumbbell-like double-hairpin. Referring to FIG. 17, upon the binding of input A, a duplex forms, to which the output strand can bind as the triplexing strand. Similarly, input B forms a duplex with the other half of the gate strand, to allow for the binding of another triplexing domain of the output. Upon the binding of both A and B, the output is constrained as a bulge loop, thus inactivating the active domain $X_{R3}$.

Referring to FIG. 18, an exemplary Hoogsteen-reverse gate, is provided. A triple-helical formation can actually be achieved in one of two ways, via the formation of Hoogsteen bonds, or reverse-Hoogsteen bonds. The difference lies in the orientation of the triplexing strand, and various solution conditions (such as pH, salt concentration, etc) affect the relative thermodynamics of the two. Both ways are approximately equally energetic, but possess different sequence requirements. By using both a Hoogsteen domain and a reverse-Hoogsteen domain, the output strand can be stretched more taut, and thus further inactivate the functional domain. Unlike the previous two gates, this gate design takes inputs in parallel—that is, either A or B can bind first. This has the effect of enforcing input equality. In a serial gate, some inputs may be more important than others, due to possible false positives. Also, the functional design of this case places no limit on the size of the toehold domains, thus there is no theoretical limit on the number of different gates of this type that can simultaneously be in solution.

Triple-helix formation, however, is substantially slower than most other processes (such as double-helix hybridization, three-way branch migration, and four-way branch migration). There is no clear extension to arbitrary numbers of inputs. Finally, use of triple helical domains place stringent sequences requirements on the DNA strands, increasing chances of crosstalk.

The function of an exemplary gate can be understood in terms of base pairing and breaking allowing efficient construction of new gates following design principles provided herein. As previously noted, an exemplary gate can include two to four short (36 nt-57 nt) oligonucleotides (see FIG. 19, panel A). One strand is the output strand: it either serves as an input to a downstream gate (see below) or has a dye-label such that its release from the gate can be detected in a fluorescence experiment. The remaining strands of the gate complex are referred to as gate strands. Both ends of the output strand (see FIG. 19, panel A), or only one end (see translator gates in FIG. 20), can be attached to the gate complex. FIG. 19, panel A, shows a three input AND-gate assembled from an output strand and three gate strands. A calculation is initiated through the addition of a set of single stranded inputs to a solution containing the gate. Each gate strand contains a recognition region which is complementary to an input. In a gate, initially the recognition regions of all gate strands, except for the gate strand furthest away from the output strand, are double-stranded and can not interact with the inputs. Only the toe-hold part of the recognition region of the first gate strand is single-stranded (3'-end of strand D in FIG. 19, panel A and panel B, blue). This region serves as a toe-hold for binding of an input strand; after binding to the toe-hold, the input can displace the gate strand from the gate complex by three-way branch migration (see FIG. 19, panel B). This strand displacement reaction is essentially irreversible since there are no toe-holds to initiate the reverse reaction. The displacement of the first gate strand leads to the exposure of the toe-hold for the subsequent input (see FIG. 19, panel B). For a given gate, this sequence of events continues until the output strand is released.

The operation of an exemplary three input AND-gate is shown in FIG. 19, panels D and E. For fluorescence experiments, a dye-labeled output strand $A_f$ was used and strand $B_q$ was labeled with a quencher (see FIG. 19, panel C). Fluorescence is quenched when $A_f$ is bound to strand $B_q$. Release of the output strand leads to an increase in fluorescence. The truth table for a three-input AND gate has eight entries (see FIG. 19, panel C) and all eight cases are covered in the three fluorescence traces shown in FIG. 19, panel D. The electrophoresis gel of FIG. 19, panel E, provides an alternative test of the gate operation that allows one to monitor not only the state of the output strand (bound vs. unbound) but also allows one to visualize reaction intermediates and waste products. Every lane of the gel corresponds to one entry in the truth table. The gates used in the present experiments were purified from a nondenaturing gel before use (see supplementary information for details on gate preparation and purification). Without purification, gate operation was considerably less reliable and some degree of signal increase was typically observed even if only a subset of inputs was present (see FIG. 22).

Figure 20:
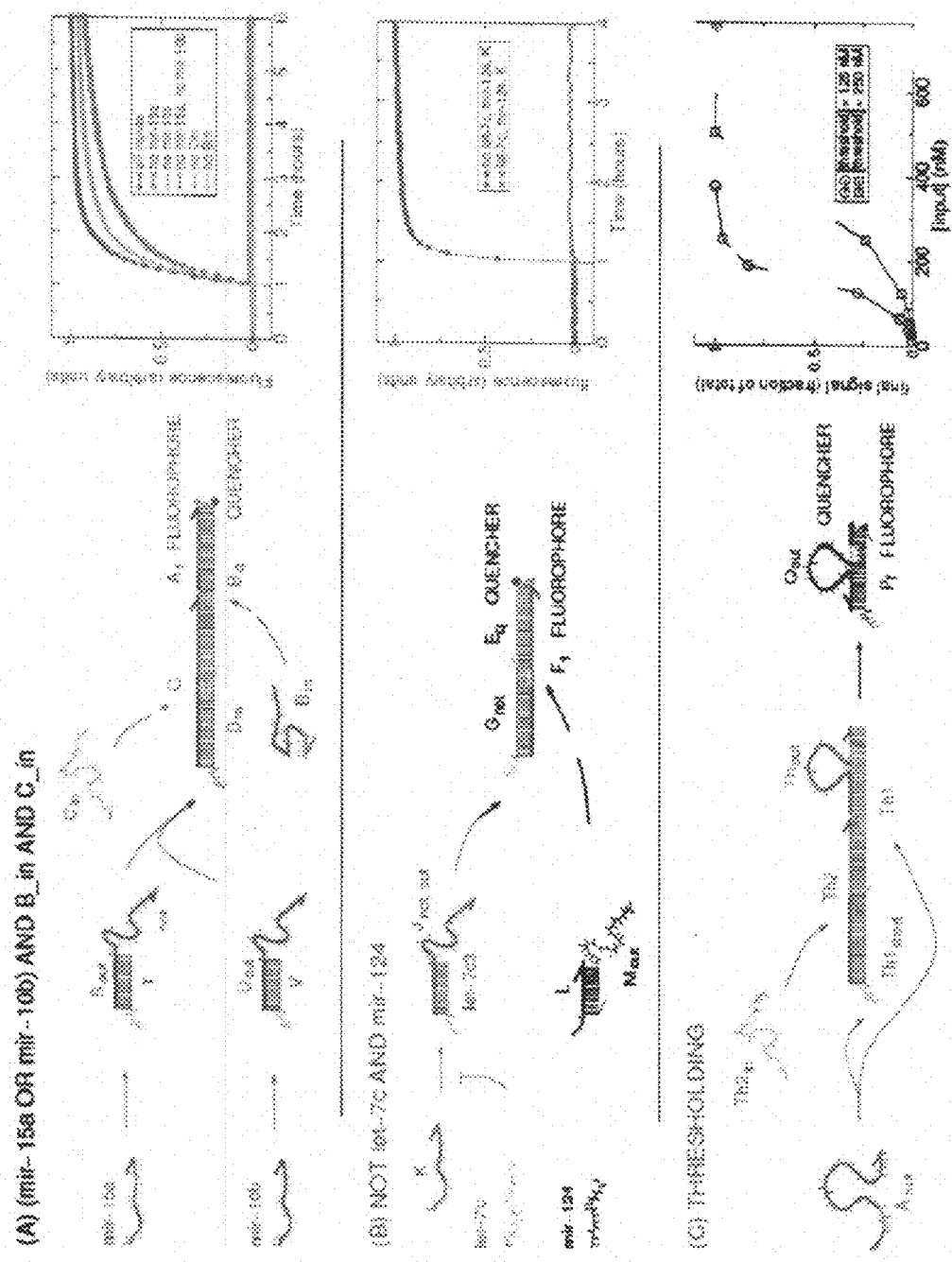
FIG. 20, panels A-C depict sequence translation, logic operations and signal restoration of an exemplary gate.

Information exchange between gates occurs through release and binding of messenger strands (the output strand of one gate may be an input strand of the downstream gate). Of the output strand, only the recognition region binds the downstream gate. Before the output strand is released, the sequence complementary to the toe-hold of the downstream gate (red FIG. 19, panel A) is double stranded, while the rest of the recognition region is single-stranded. Since in the downstream gate only the toe-hold will be single-stranded, protecting the toe-hold binding region in the upstream output is sufficient to avoid reactions between bound output strands and downstream gates. Thus the sequence of the recognition region, except for the toe-hold, is independent of any of the inputs to the gate. This permits the logical separation of inputs and output signals by avoiding cross-talk between them. To obtain complete sequence independence including the toe-hold, a full-translator can be used, as described below:

A three-gate circuit that demonstrates logical AND and OR, cascading, and sequence translation, operates as designed with minimal leak (FIG. 20, panel A). The circuit is composed of translator gates and an AND gate of the kind introduced in FIG. 19. A translator is an AND gate with a single input (it is logically equivalent to a repeater gate), and its function can be to translate the signal encoded in the input messenger strand to a signal encoded in the output messenger strand. The two translator gates UV and ST in the circuit of FIG. 20, panel A, translate two different biological micro RNA sequences (mir-15a and mir-10b from mouse respectively) into outputs with identical recognition regions. In the circuit of FIG. 20, panel A, the two translators are used to implement a logic OR. The input to a translator gate and the recognition region of the output strand do not need to share any sequence except for the toehold region, where they can be the same. However, if the output of one translator gate is used as an input to another translator gate, then there is no sequence restriction between the initial input messenger strand and the output messenger strand of the last translator. The resulting component is called a full translator. The cascade of the two gates NO and HI provides an example of such a full translator (see FIG. 21 and FIG. 23). Generally, translators are useful in connecting subcircuits that do not a priori use the same sequences for the toe-hold and recognition regions, which is especially useful for adapting an existing circuit to act on arbitrary biological input.

To demonstrate a NOT operation on an input, a circuit was constructed that calculates the logical expression (NOT let-7) AND mir-124 (see FIG. 20, panel B). To invert an input, an additional strand is needed. This inverter strand is complementary to the input. A NOT gate is a repeater gate for the inverter strand. If the input is present, it will bind the inverter strand and prevent the activation of the repeater gate. Otherwise, if the input is absent, the inverter strand activates the repeater gate. In the example circuit of FIG. 20, panel B, the inverter strand is labeled K and is the complement to input let-7c. This type of NOT operation can only be applied to external inputs rather than output messenger strands. Even inactive output strands have large single stranded regions and could therefore bind their inverter strands. Given an arbitrary Boolean circuit consisting of AND, OR and NOT gates, the NOT gates can always be "pushed" into the layer immediately accepting the input without increasing the size of the circuit by more than a factor of two. The resulting circuit effectively converts the input signals into the dual-rail representation at the first level and then proceeds to compute using dual-rail logic.

Figure 24:
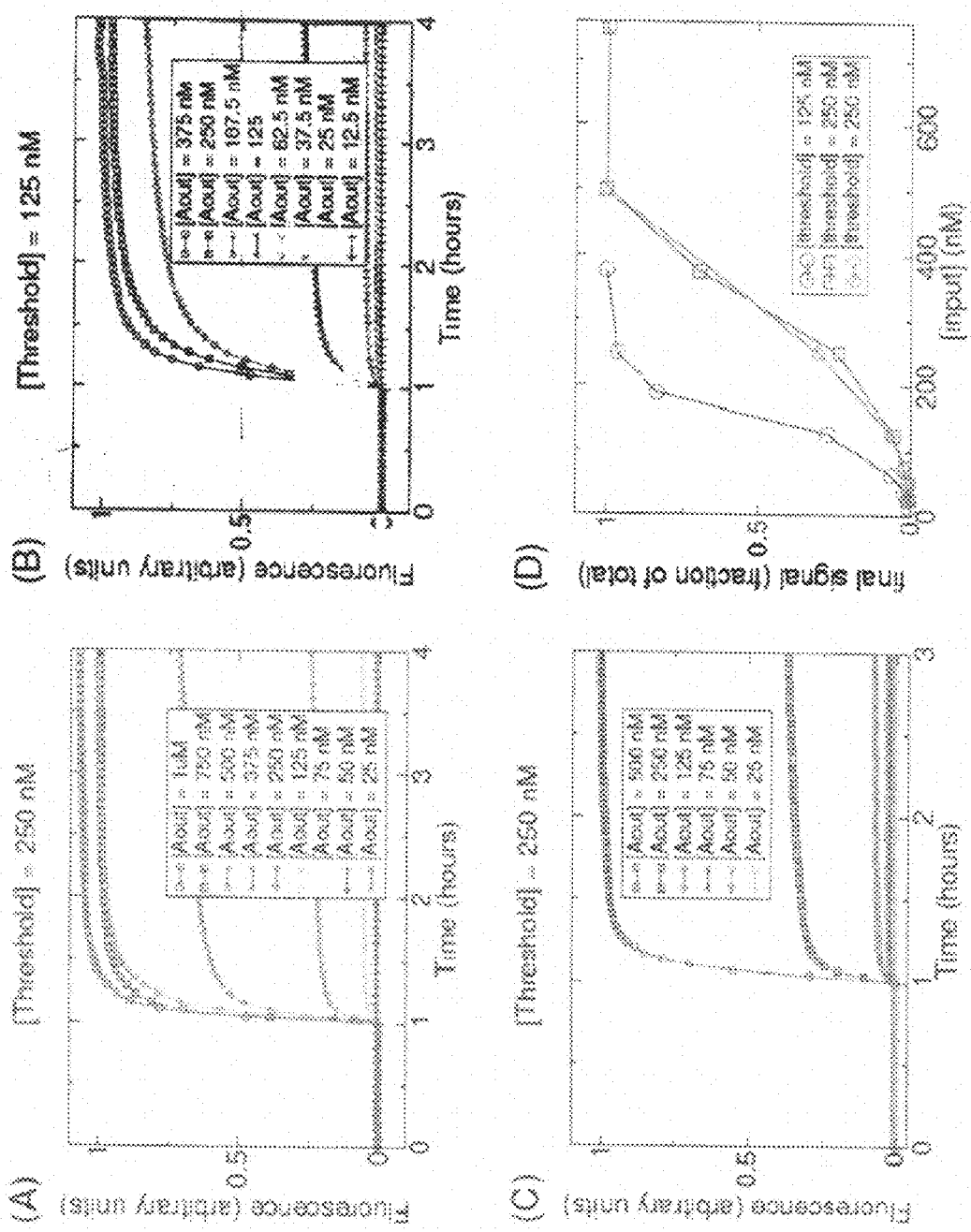
FIG. 24. panels A-D, depict fluorescence data for the threshold circuit of FIG. 20, panel C.

There are two general ways that a gate may not perform as desired. First, it may fail to produce the expected amount of output strand. Second, it may occasionally "leak" by spontaneously releasing the output strand. Both types of error require signal restoration; in the first case by increasing a moderate output amount to the full activation level, and in the second case by decreasing a small output A amount to an insignificant level. In order to achieve this, gates for amplification and thresholding were developed. The threshold gate (FIG. 20, panel C) is a three-input AND gate with identical first and third inputs. The second input is always present in solution and can be considered part of the thresholding unit. It is necessary for structural purposes only and serves no computational function. In the presence of a sub-stoichiometric amount of input (less than the total concentration of threshold gates), most gates will lose only their first and second gate strands—thus releasing no output. Whereas for input concentrations greater than twice the concentration of the threshold gates, most gates will produce output. Thus, the threshold gate concentration serves as a threshold (FIG. 20, panel C, and FIG. 24). However, since the output of the threshold gate cannot exceed half the input signal, subsequent amplification is necessary.

Figure 21:
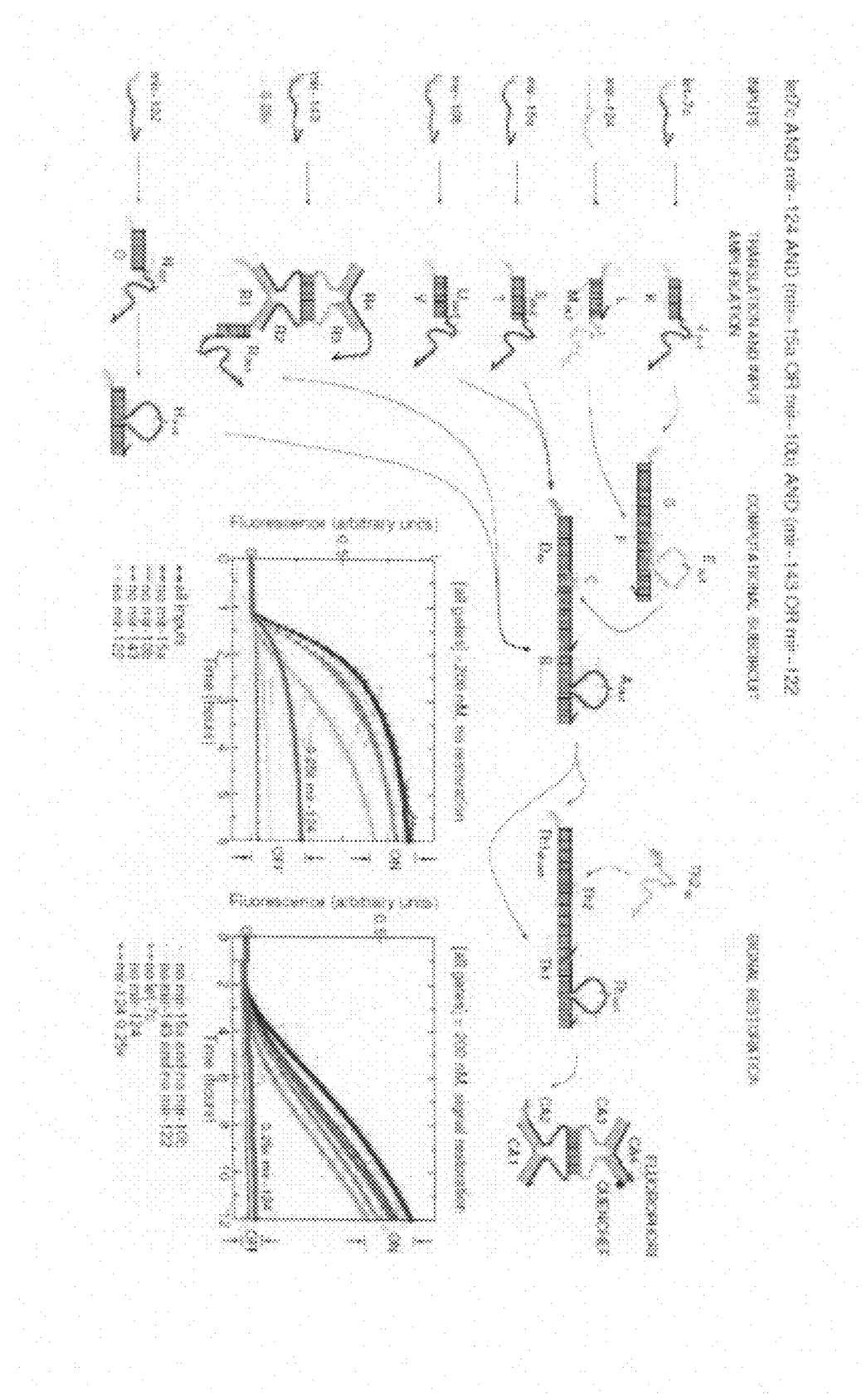
FIG. 21 depicts signal propagation through a chemical circuit combining AND, OR sequence translation, input amplification and signal restoration.

A hybridization-based system for catalytic amplification is known to those skilled in the art. With minor modifications, the hybridization-based system serves both as an input amplifier and as a full translator (FIG. 21, left, mir-143 translator). A single input strand can catalytically trigger the release of several output strands; initially the concentration of output strand increases linearly with time, with a slope that is proportional to the amount of input strand. If no output messenger strand is required, because the output is to be monitored by fluorescence, then a simpler version of the catalytic amplifier can be used (FIG. 25, panel A. and FIG. 21, right). Alternatively, amplifiers based on feedback logic can be designed. FIG. 25, panel B, shows a two-gate feedback circuit that amplifies the fluorescence output signal without producing an output messenger strand. It consists of two translators such that the output of the first acts as an input for the second and the output of the second acts as input for the first. The fluorescence amplifier also amplifies the output signal linearly with time. This simple example indicates that the gates provided herein can be used to construct arbitrary feedback circuits; amplifiers based on feedback circuit properties have great potential for sophisticated function, such as exponential amplification.

When the threshold gate feeds into an amplifier gate (as in FIG. 21), the sigmoidal activation curve of the threshold gate ensures that small "leak" signals are minimized, while sufficiently strong signals are restored to an output level roughly comparable to the total amplifier gate concentration. Thus, these two gates together constitute a signal restoration module. The incorporation of the threshold gate and the amplifier gate in a large circuit at multiple intermediate points ensures the stability of digital abstraction over the many layers of the circuit.

Figure 29:
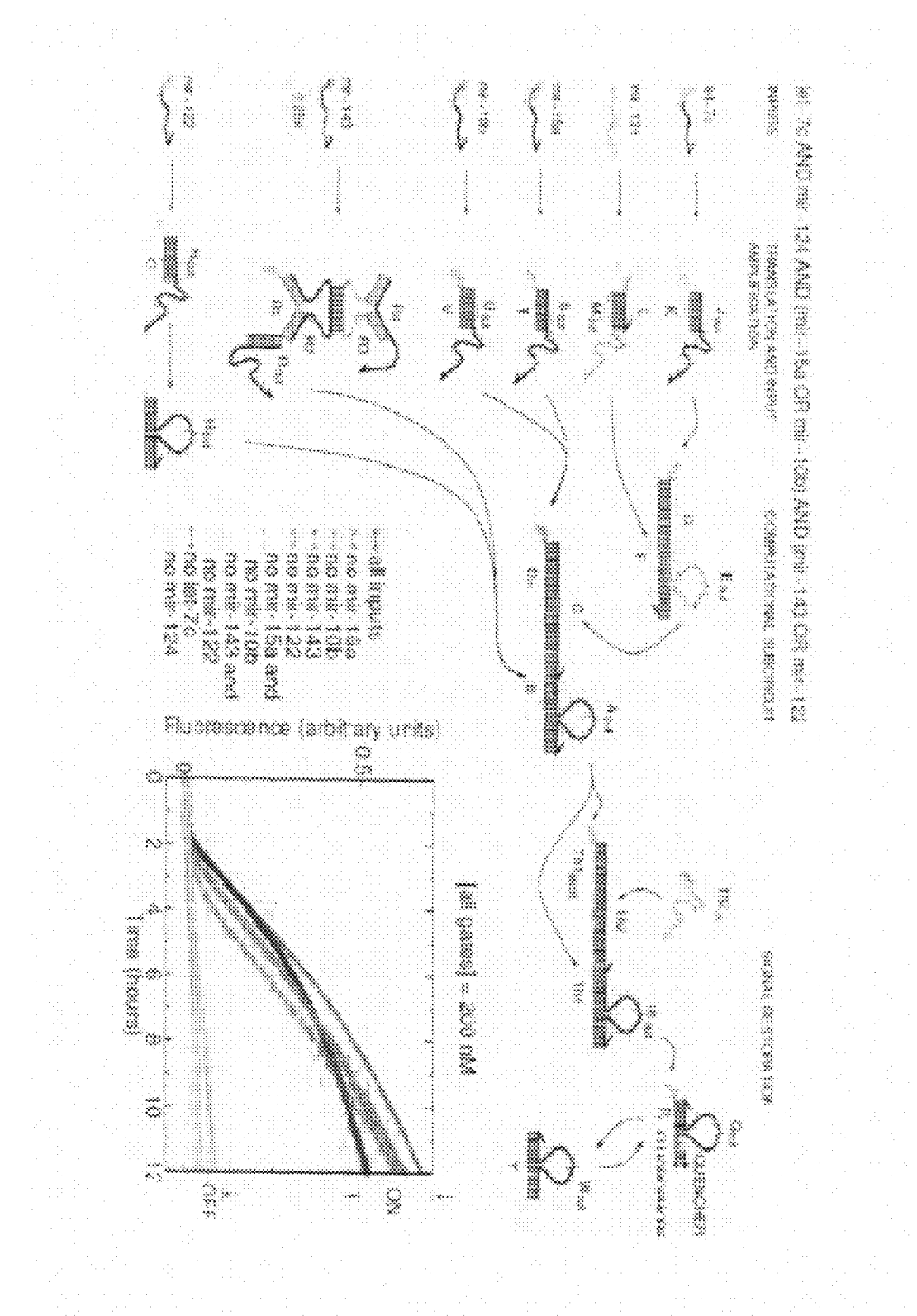
FIG. 29 depicts a circuit with a feed-back amplified output.

Finally, to demonstrate modularity and scalability eleven gates were combined into a larger circuit. The circuit combines previously introduced modules for input translation and amplification, the calculation of AND, OR, and signal restoration (see FIG. 21). The inputs to the circuit are six different mouse micro RNAs, namely let-7c, mir-124, mir-15a, mir-10b, mir-143, and mir-122. Although the data shown (FIG. 21, inset) are obtained using synthetic DNA oligonucleotides in purified solutions, separate experiments show that the present gates can be also activated by RNA inputs and still function in the presence of total mouse RNA (see e.g., FIG. 26). To determine the effectiveness of signal restoration, an equivalent circuit without the signal restoration module was constructed and tested for both circuits with an input at 0.25× to simulate a large upstream leak. In contrast to the circuit without signal restoration, whose output reached 25%, the complete circuit was able to maintain a low output signal (FIG. 21, inset). To verify the correct operation of other circuit components, several subcircuits were constructed and tested independently (FIG. 27 and FIG. 28). The feedback fluorescence amplifier was tested as a replacement for the catalytic amplifier at the output, resulting in a circuit containing 12 gates (FIG. 29).

As increasingly larger circuits are constructed, speed becomes a limiting factor for circuit operation. The circuit without signal restoration takes 2 hours to half activation (FIG. 21, inset, left). The circuit including signal restoration has two additional layers and takes 10 hours to achieve half activation (FIG. 21, inset, right). Having said that, in both cases a clear difference between off and on states can be established considerably earlier. Speeding up the responses of individual gates may improve overall circuit performance. Shortening the recognition regions of a gate and messenger strands should permit the construction of faster gates, since the duration of branch migration scales quadratically with the number of base pairs a affected. However, the recognition regions must be long enough to avoid spontaneous dissociation of the gate complex.

Construction of the circuits provided herein can be attributed to four main principles and practices: 1) adherence to the tenets of digital logic; 2) toehold sequestering combined with branch migration and strand displacement; 3) reduction of leak reactions by identifying and purifying functional from malfunctional gate complexes; and 4) modularity of design that allowed easy re-wiring and composition of circuits. The logic gates developed here are compatible with other approaches to building molecular automata in vitro and in vivo, either as full modular components or as design principles. Since evidence suggests that the present logic gates can use natural RNA as input, and that they function correctly in the presence of mouse total RNA, the hybridization-based circuits might be adopted for in situ detection of complex expression patterns or even in vivo logic processing.

For microRNA translator gates, the length of the gate strand recognition region is determined by the length of the microRNA input and ranges from 20 to 22 nt. Toe-holds for input binding are six nucleotides long. The recognition region of the output strand is 36 nucleotides (nt) long of which 27 nt are single-stranded before output release. The double stranded (9 bp) part of the recognition region includes the toe-hold binding sequence (6 nt) and a protecting three base-pair clamp. In all other gates, recognition regions for both input and output strands are 36 nt long. The first gate strand in any AND gate as well as the gate strands in gates HI, $Q_{out}P_f$, and WY thus are 36 mers. Additional gates strands are 60 mers. Output strands are 57 mers. Before release, output strands are bound to their gate with both ends. The two binding regions are 15 base pairs long while the single stranded loop region has length 27 nt. For design details, see FIG. 22.

DNA oligos were synthesized and purified by Integrated DNA Technologies, Coralville, Iowa. DNA stock solutions were prepared at a concentration of 50 μM in ultra (pure water (purified by a Milli-Q system, Millipore, Bedford, Mass.). Concentrations were determined from the measured absorbance at 260 nM and the calculated extinction coefficient (calculation based on the nearest-neighbor model.

RNA oligos with sequences identical to biological microRNAs mir-124 and let-7c were also synthesized and purified by IDT. Mouse brain and liver total RNA samples were obtained from Ambion, Inc., Austin, Tex. Dye labels were used to follow reaction kinetics: Carboxytetramethylrhodamine (TAMRA) was used as a fluorophore and Iowa Black $R_Q$ as a dark quencher. Even though the same fluorophore was used in all experiments and all dye-labeled strands were ordered HPLC purified, fluorescence intensity was observed to vary strongly between strands with different sequences and between different batches of the same strand.

TAE/Mg$^{++}$ buffer (0.04 M Tris Acetate, 1 mM EDTA, 12.5 mM Mg Acetate, pH 8.3) was used for all reactions including fluorescence experiments, formation gels and gel elutions for purification.

Gel Electrophoresis: Non-denaturing polyacrylamide gels (acrylamide-bis 19:1, 8%, 2-3 h at 15 V/cm, and 4° C.) were used to verify structure formation and to analyze reaction mixtures. For imaging, gels were stained with SybrGold (Molecular Probes, Eugene, Oreg.) for 35 min, excited at 488 nm and imaged with 530 bandpass filter on a Bio-Rad (Hercules, Calif.) Molecular Imager FX Pro Plus.

Gate Formation and Purification: Gates were formed in a slow anneal where the reaction mixture is heated up to 90° C. and then slowly (1° C./min) cooled down to room temperature. Each gate sample was formed in a separate reaction.

For purification, gates were prepared at 10 or 20 μM. In initial experiments gates were purified from a gel directly after annealing. Gel elution (4-5 h at 15 V/cm and 4° C.) was done using the Elutrap Electroelution System (Schleicher and Schuell Biosience, Dassel, Germany). Purification allowed for the separation of fully from partially assembled structures and dramatically decreased leak signals due to false triggering in fluorescence experiments. However, false triggering could not be completely eliminated with this approach, probably because gates with only minor defects (e.g. gates containing incorrectly synthesized strands with only a few bases missing) co-migrate with the error-free gates in the gel.

In order to at least partially eliminate gates with minor defects, an improved purification scheme was developed. In this approach, gates were incubated with their inputs overnight at room temperature before purification. Importantly, first-acting inputs were truncated such that they would not react with correctly formed gates. Specifically, toe-hold binding regions were removed from inputs targeting gate strands with a single stranded toe-hold, i.e. the first input in an AND gate and inputs to translator gates. (For translator gates taking microRNA input, in addition to truncating the toe-hold, the strand was extended by 3 nt to cover the 3 nt clamp shown in FIG. 22). Second and third inputs to AND gates need not be truncated: in fully assembled gates, all regions that could potentially bind them are double stranded. Correctly formed gates assembled from full length strands should not react with these truncated inputs. However, malformed gates or gates containing strands with synthesis errors can potentially react with these inputs. Inputs were added at substoichiometric concentrations between 5 or 10 μM per input. After incubation, purification proceeded as described above. Incubation with inputs suppressed leak signal further, in some cases to undetectable levels (see FIG. 23).

After purification the effective concentrations of the gates were estimated from a measurement of the absorbance at 260 nm and the calculated extinction coefficients for the gates. The extinction coefficient for a gate was approximated by the sum of the extinction coefficients of its constituent segments (loops, toe-holds, double-stranded sections or dye labels, where present). Extinction coefficients were calculated independently for all the single stranded (e.g. toe-hold and loop-regions) and double stranded segments. The extinction coefficients $e_{ds}$ for the double stranded sections were calculated using the phenomenological expression:

$$e_{ds} = e_{ss}(seq) + e_{ss}(seq) - 3200 \times N_{AT} - 2000 \times N_{GC}$$

Here $e_{ss}$(seq) is the extinction coefficient of one component strand in the duplex in its single stranded state, $e_{ss}$(seq) is the same for complementary sequence in the duplex and $N_{AT}$ and $N_{GC}$, respectively, are the number of AT- and GC-pairs in the duplex. The magnitude (per base pair) of the negative correction to the extinction coefficient of a duplex was estimated from techniques known to the skilled artisan. The extinction coefficients for the fluorophore and quencher provided by IDT were used (TAMRA: e=29100, Iowa Black RQ: e=50457).

Kinetics Measurements and Fluorescence data Normalization: The experiments for FIG. 26, panel C, were performed on a SPEX Fluorolog-3 (Jobin Yvon Horiba, Edison, N.J.), with excitation at 559 nm (2 nm bandwidth) and emission at 583 nm (10 nm bandwidth), recorded every 30 seconds. All other kinetics experiments were done in a fluorimeter custom built by Bernard Yurke. The fluorophores were excited at 532 nm and emitted fluorescence intensity was integrated from 550 nm to 600 nm. Fluorescence experiments were performed with each reaction volume of 100 µl maintained at 25° C. and reactant concentrations ranging from 10 nM to 1 µM. Gates were mixed in a test-tube before the start of each experiment with one dye/quencher-labeled gate serving as a read-out.

In a typical experiment, four samples were run in parallel and one data point (per sample) was acquired every second. Of the four instrument channels available, one was used for measuring a reference sample and only three were used for kinetics experiments. The reference sample contained a single dye-labeled strand of DNA and was prepared afresh at least every two days (to compensate for photo bleaching and sample loss due to evaporation). The signal strength of the reference sample should remain constant in the absence of noise, so measuring a reference allowed monitoring fluctuations in laser intensity and other sources of (channel-independent) instrument noise.

The four instrument channels were not completely identical and the signal strength varied between the four channels. Differences were either due to uneven splitting of the exciting laser light between the four samples, scattering effects along different optical paths or, due to variations in amplification or detection efficiencies between photo-diode detectors. These channel-to-channel variations were maximally on the order of 35% and were found to be constant on time-scales relevant for the experiments.

The raw experimental data was corrected for these channel to channel variations as follows: At the end of each experimental run, all four samples (including the reference) were removed and then, in turn, moved to the same instrument 1 channel where the signal was recorded for 1-5 minutes. In addition, the cuvette containing the reference sample was moved to the three slots used for kinetics experiments and the signal strength was recorded for 1-5 min.

Either set of measurements allowed subsequent adjustment of the raw data for channel-to-channel variations, and both methods gave equivalent results.

The amount of instrument noise varied between experiments. For most of the data shown in this paper, noise did not exceed 1% of the signal. However, noise up to 10% of the signal was not unusual. In situations where noise was clearly correlated between all four channels (most probably noise to laser intensity fluctuations), experimental data was divided by the reference signal in order to correct for this noise.

Initial fluorescence was measured for at least one hour before inputs were added, in order to determine the fluorescence base-line and also to make sure that the read-out gate was not triggered spontaneously due to spurious interactions with other gates in solution. Initial fluorescence due to incomplete quenching was typically on the order of or less than 5% of the final signal. However, on rare occasions, the initial signal could be as high as 15-20% of the final signal. In cases where the read-out gate was not fully triggered at the end of an experimental run (e.g. because of slow kinetics) the read-out gate was triggered explicitly by addition of extra inputs and the final value was recorded. Data was subsequently normalized such that the signal measured before addition of inputs corresponded to zero while the signal of the fully triggered read-out gate corresponded to one.

All data was shifted such that the time of input addition corresponds to time t=1 hour in order to make comparison of the reaction kinetics between different fluorescence traces easier.

Except where constrained by biological sequences or pre-existing DNA devices, all sequences were design by computer optimization. In the design process, the main structural constraints were imposed from the outset, such as domain lengths and complementarity requirements. In particular, recognition regions of output gate strands must be complementary to their target and each gate strand must be able to correctly bind its neighboring gate strand(s). In some cases, double-helical domains were terminated by G-C pairs to reduce fraying. Input strand sequences were entirely determined by sequence of their target gate strand. Sequences were designed incrementally as the research progressed; in each design stage, strand sequences from the previous stages constrained choices for the new gate sequences.

In each stage, a set of random sequences obeying these structural constraints are then generated and an iterative optimization scheme is applied to them. The optimization process allows one to implement a set of additional soft constraints. These included: (i) minimization of secondary structures in single-stranded species (the input and messenger strands), as predicted by the minimum-free-energy (MFE) structure at 25° C. using DNA parameters; (ii) minimization of cross-talk between all single-stranded species, as measured by the ΔG of association between pairs of strands (estimated as intramolecular MFE for a 'virtual' strand linking the two sequences via 5 unpaired nucleotides); (iii) especially avoiding secondary structure in messenger strands and single-stranded portions of partially-triggered gates that hides the toe-hold binding region; (iv) avoiding a set of undesired sequences (e.g. more than three consecutive repeats of the same base); (v) minimizing the occurrence of short subsequences (3 to 10 base pairs) that have exact or near-exact complementary matches elsewhere either in the same strand or in other strands, except as intended by design (generally referred to as sequence symmetry minimization; (vi) making all toe-holds of similar strength (predicted ΔG at 25° C.); (vii) avoiding branch migration of the bulge loop region in a bound output strand: this is achieved by imposing that the first four single-stranded nucleotides at the base on one side of the loop are different from the last four nucleotides in the double stranded region directly adjacent to the loop on the other side. Scores for each of these soft criteria were weighted and summed to obtain an overall score for the set of sequences being designed. Sequence optimization proceeded by random descent to minimization of the overall score: sequence mutations were made randomly (subject to satisfying the structural constraints) and accepted if the score was reduced. If the final sequences were unsatisfactory, the scoring weights were adjusted, new initial sequences were chosen, and optimization was attempted again.

A set of toe-holds was designed in the first stage, then the ABCD gate was designed, then the WY and PQ gates, then the EFG gate and most translators (including the full translator, but excluding UV and ST), and finally the UV and ST translators (whose microRNA targets were chosen to share a 6 nt toe-hold domain) were designed to demonstrate implicit OR. The catalytic amplifiers CA and R were designed by cutting-and-pasting appropriate recognition domains into the molecules. Similarly, the sequences for the threshold gate were entirely defined by pre-existing sequences.

If the amount of $A_{out}$ is small, and thus threshold gates remain mostly unreacted, then the probability that a single threshold gate reacts with two molecules of $A_{out}$ is roughly quadratic in the amount of $A_{out}$. Consequently, in this regime, the relationship between Aout and the amount of triggered threshold should be approximately quadratic. If the amount of $A_{out}$ is large and most of the threshold gate has reacted with $A_{out}$ at least once, then there is a linear relationship between $A_{out}$ and the amount of triggered threshold, until $A_{out}$ is greater than twice the amount of threshold where saturation is observed. A simple two equation model is sufficient to approximately explain the resultant sigmoidal transfer function over the entire input range (a single parameter fit matches the data of FIG. 20, panel C and FIG. 24, panel D, to within @ 10%):

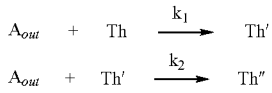

$$A_{out} + Th \xrightarrow{k_1} Th'$$
$$A_{out} + Th' \xrightarrow{k_2} Th''$$

where Th, Th', and Th" represent three states of the threshold gate, with the last state being triggered. (Including the intermediate reaction with $Th2_{in}$ is necessary for greater physical plausibility but the principle of the operation of the threshold gate can be explained without it.) A larger threshold gate taking n>2 molecules of $A_{out}$ as input should provide a better than quadratic non-linearity: using the above intuition, the transfer function should be of power n for low amounts of $A_{out}$.

TABLE I

Exemplary gates, gate strands, inputs and outputs.

| Gate | input 1 | input 2 | input 3 | gate strands | output | ext. coeff. |
|---|---|---|---|---|---|---|
| ABCD | $D_{in}$ | $C_{in}, E_{out}$ | $B_{in}, H_{out}$ | D, C, B | $A_{out}$ | 1847480 |
| $A_fB_qCD$ | $D_{in}$ | $C_{in}, E_{out}$ | $B_{in}, H_{out}$ | D, C, $B_q$ | $A_f$ | 1677057 |
| $ABCD_m$ | $D_{m. in}, S_{out}, U_{out}$ | $C_{in}, E_{out}$ | $B_{in}, H_{out}, R_{out}$ | $D_m$, C, B | $A_{out}$ | 1869280 |
| $A_fB_qCD_m$ | $D_{m. in}, S_{out}, U_{out}$ | $C_{in}, E_{out}$ | $B_{in}, H_{out}, R_{out}$ | $D_m$, C, $B_q$ | $A_f$ | 1678177 |
| EFG | $J_{out}$ | $M_{out}$ | | G, F | $E_{out}$ | 1378540 |
| $E_qF_fG$ | $J_{out}$ | $M_{out}$ | | G, $F_f$ | $E_q$ | 1183277 |
| $E_qF_fG_{not}$ | $J_{out, not}$ | $M_{out}$ | | $G_{not}, F_f$ | $E_q$ | 1180697 |
| JK | let-7c | | | K | $J_{out}$ | 622000 |
| $JK_{not}$ | K | | | let-7c3 | $J_{out, not}$ | 598380 |
| LM | mir-124 | | | L | $M_{out}$ | 624880 |
| NO | mir-122 | | | O | $N_{out}$ | 669860 |
| HI | $N_{out}$ | | | I | $H_{out}$ | 851040 |
| PQ | $A_{out}, W_{out}$ | | | P | $Q_{out}$ | 907317 |
| input amp. | mir-143 | | | $R_1, R_2, R_3, R_4$ | $R_{out}$ | — |
| ST | mir-15a | | | T | $S_{out}$ | 625300 |
| UV | mir-10b | | | V | $U_{out}$ | 619180 |
| WY | $Q_{out}$ | | | Y | $W_{out}$ | 825140 |
| threshold | $A_{out}$ | $Th2_{in}$ | $A_{out}$ | $Th1_{short}$, Th2, Th1 | $Th_{out}$ | 1874440 |
| signal amp. | $Th_{out}$ | | | CA1, CA2, CA3, CA4 | — | — |

TABLE II

Input strand sequences. All exemplary toe-holds and exemplary toe-hold binding regions are shown in gray, while recognition regions (including toe-holds) are underlined.

| Strand | sequence (SEQ ID NOs:1-19) |
|---|---|
| $B_{in}$ | TTGGAGGTGTTTATAGCGGACCCCTACTGAGTTGTG |
| $C_{in}$ | CTCCAAGAGTGATATGCCAATACAAACCACGAAGAC |
| $D_{in}$ | CGGTTTCACATTACTTTTGCTGCCTTACGAGTCTTC |
| $D_{m, in}$ | TTTGTGCACATTACTTTTGCTGCCTTACGAGTCTTC |
| $D_{in}$-no-toe | CACATTACTTTTGCTGCCTTACGAGTCTTC |
| let-7c | TGAGGTAGTAGGTTGTATGGT |
| let-7c-no-toe | AGTAGGTTGTATGGTTGT |
| mir-124 | TAAGGCACGCGGTGAATGCC |
| mir-124-no-toe | GATTAAGGCACGCGGTC |
| mir-15a | TAGCAGCACATAATGGTTTGTG |
| mir-15a-no-toe | CACATAATGGTTTGTGCAC |
| mir-10b | CCCTGTAGAACCGAATTTGTGT |
| mir-10b-no-toe | AGAACCGAATTTGTGCAC |
| mir-122 | TGGAGTGTGACAATGGTGTTTG |
| mir-122-no-toe | GTGACAATGGTGTTTGGAT |
| mir-143 | TGAGATGAAGCATGTAGCTCA |
| $G_{in}$-no-toe | TGTTTATCTGTTCCCTGATCTTTAGCCTTA |
| $I_{in}$-no-toe | GATGAATTGGAGGTGGGATATTATTACTGA |
| $Th2_{in}$ | CGCTATCTGACTGACTGTTACCGATTTGTTTCATTC |

TABLE III

Gate and output exemplary strand sequences. Dye and quencher positions are indicated: TAM stands for TAMRA (NHS Ester) and IB RQ for IowaBlack RQ. All toe-holds and toe-hold binding regions are shown in gray and recognition regions (including toe-holds) are underlined.

| Strand | sequence (SEQ ID Nos:1-64) |
|---|---|
| A | GTGTTTATAGCGGACTGACGGTTTCACTACCCTGTTGTTCTACCCTACTCAGTTGTG |
| $A_{out}$ | GTGTTTATAGCGGACTTACTAGATTTATACCCTGTTGAATGACCCTACTGAGTTGTG |
| $A_f$ | GTGTTTATAGCGGACCCCTACTGAGTTGTG/TAM/ |
| B | CACAACTCAGTAGGGGTCCGCTATAAACACCTCCAAGAGTGATATGCCAATACAAACCAC |
| $B_q$ | /IB_RQ/CACAACTCAGTAGGGGTCCGCTATAAACACCTCCAAGAGTGATATGCCAATACAAACCAC |
| C | CACATTACTTTTGCTGCCTTACGAGTCTTCGTGGTTTGTATTGGCATATCACTCTTGGAG |
| D | GAAGACTCGTAAGGCAGCAAAAGTAATGTGAAACCG |
| $D_m$ | GAAGACTCGTAAGCCAGCAAAAGTAATGTGCACAAA |
| $E_{out}$ | GTTAGATGTTAGTTTCTCCAAGAGTGATATGCCAATACAAACCACGAAGACAATGAT |
| $E_q$ | /IB_RQ/GTTAGATGTTAGTTTCACGAAGACAATGAT |
| F | TGTTTATGTGTTCCCTGATCTTTAGCCTTAATCATTGTCTTCGTGAAACTAACATCTAAC |
| $F_f$ | TGTTTATGTGTTCCCTGATCTTTAGCCTTAATCATTGTCTTCGTGAAACTAACATCTAAC/TAM/ |
| G | TAAGGCTAAAGATCAGGGAACACATAAACAACCATA |
| $G_{not}$ | TAAGGCTAAAGATCAGGGAACACATAAACATGACGT |
| $H_{out}$ | GATGAATTGGAGGTGTTTATAGCGGACCCCTACTGAGTTGTGGGATATTATTACTGA |
| I | TCAGTAATAATATCCCACCTCCAATTCATCCAAACA |
| $J_{out}$ | AGTAGGTTGTATGGTTGTTTATGTGTTCCCTGATCTTTAGCCTTA |
| $J_{out,\ not}$ | CAACCTACTACCTCATGTTTATGTGTTCCCTGATCTTTAGCCTTA |
| K | ACAACCATACAACCTACTACCTCA |
| let-7c3 | ACATGAGGTAGTAGGTTGTATGGT |
| L | GGCATTCACCGCGTGCCTTAATC |
| $M_{out}$ | GTTAGATGTTAGTTTCACGAAGACAATGATTAAGGCACGCGGTG |
| $N_{out}$ | GTGACAATGGTGTTTGGATGAATTGGAGGTGGCATATTATTACTGA |
| O | ATCCAAACACCATTGTCACACTCCA |
| $P_f$ | AACAGGGTAACTCAGGAACAGGTCCGCTATGTCAGG/TAM/ |
| $Q_{out}$ | /IB_RQ/CCTGACATAGCGGACTGACGGTTTCACTACCCTGTTGTTCTACTGTTCCTGAGTTAC |
| $R_1$ | CACCTCCAATTCATCAATGAGGGTGACTTCTGAGCTACAGTCCTTCATCTCA |
| $R_2$ | GAAGCACTGTAGCTCACACACAGTAGATCAGAATTGGCACGTTCGCTCGCTAGGTTGAAGTCACCCTCATT |
| $R_3$ | ATCAATGAGGGTGACTTCAACCTAGCGAGCGAACGTGCCAATTCTGATCTACTGTGTGTGAGCTACAGTGCTTCA |
| $R_4$ | TGAAGCACTGTAGCTCAGAAGTCACCCTCATTGATGAATTGGAG |
| $R_{out}$ | GATGAATTGGAGGTGTTTATAGCGCACCCCTACTGAGTTGTG |
| $S_{out}$ | CACATAATGGTTTGTGCACATTACTTTTGCTGCCTTACGAGTCTTC |
| T | GTGCACAAACCATTATGTGCTGCTA |
| $U_{out}$ | AGAACCGAATTTGTGCACATTACTTTTCCTGCCTTACGAGTCTTC |
| V | GTGCACAAATTCGGTTCTACAGGG |
| $W_{out}$ | GACTGACGGTTTCACCCTGACATAGCGGACCTGTTCCTGAGTTACCCTGTTGTTCTA |

TABLE III-continued

Gate and output exemplary strand
sequences. Dye and quencher positions are indicated: TAM
stands for TAMRA (NHS Ester) and IB RQ for IowaBlack RQ. All
toe-holds and toe-hold binding regions are shown in gray and
recognition regions (including toe-holds) are underlined.

| Strand | sequence (SEQ ID Nos:1-64) |
|---|---|
| Y | TAGAACAACAGGGTAGTCAAACCGTCAGTCCGCTAT |
| Th$_{out}$ | GACTTACTAGATTTACCTGACATAGCGGACCTGTTCCTGAGTTACCCTGTTGAATGA |
| Th1 | TCATTCAACAGGGTATAAATCTAGTAAGTCCGCTATCTGACTGACTGTTACCGATTTGTT |
| Th2 | GACTTACTAGATTTATACCCTGTTGAATCAAACAAATCGGTAACAGTCAGTCAGATAGCG |
| Th1$_{short}$ | TCATTCAACAGGGTATAAATCTAGTAAGTCCGCTAT |
| CA2 | AACAGGGTAACTCAGGAACAGCACACAGTAGATCAGAATTGGCACGTTCGCTCGCTAGGTTGAAGTCACCCTCATT |
| CA3 | /IB_RQ/AATGAGGGTGACTTCAACCTAGCGAGCGAACGTGCCAATTCTGATCTACTGTGTGCTGTTCCTGAGTTAC |
| CA1 | AATGAGGGTGACTTCCTGTTCCTGAGTTAC |
| CA4 | GTAACTCAGGAACAGGAAGTCACCCTCATT/TAM/ |

Referring again to FIG. 19, an exemplary schematic of gate operation is provided. Panel A shows a three-input AND gate consisting of four DNA strands labeled A (output strand, 57 mer), B (60 mer), C (60 mer) and D (36 mer). The 3'-ends of all strands are marked by arrows. Toe-holds and toe-hold binding regions (all 6 nt) are indicated in color. Panel B shows a calculation of logical AND of three inputs. Input strands $B_{in}$, $C_{in}$ and $D_{in}$ are 36 mers complementary to recognition regions within the corresponding gate strands B, C and D (strand D consists entirely of its recognition region). The calculation proceeds through a series of toe hold mediated strand displacement reactions. Input strand $D_{in}$ binds at the exposed toe-hold (blue) of strand D and then displaces D from the gate by three-way branch migration. In the process, waste product $DD_{in}$ is formed and a toe-hold for $C_{in}$ (cyan) becomes available. Subsequently, input $C_{in}$ releases strand C forming the $CC_{in}$-duplex. Then, input $B_{in}$ forms a duplex with strand B and the output strand Aout is released into solution. Panel C shows a Truth table for the three-input AND gate. Only if all three inputs are present the output strand will be released (entry 8). The released output strand is highlighted. Panel D shows the results of fluorescence experiments. For fluorescence experiments, strands $A_f$ (labeled with a fluorophore at the 3'-end, but without the bulge loop) and $B_q$ (quencher at the 5'-end) were used instead of $A_{out}$ and B. The gate used for fluorescence experiments is shown in the inset and fluorophore (F) and quencher (Q) positions are indicated. Fluorescence is quenched initially; an increase in fluorescence is a measure of the progress of the reaction. Inputs are added sequentially with one hour delay between additions. The order of input addition is permuted cyclically between the three fluorescence traces. In this way, all eight entries of the truth table are covered in only three experiments. In the blue trace, for example, start with the gate and no input (entry 1), then add $B_{in}$ (entry 2), then $C_{in}$ (entry 5) and finally $D_{in}$ (entry 8). The numbers in the figure refer to the entries in the truth table. Experiments are done at 25° C. at a concentration of 500 nM for all species. Panel E shows an electrophoresis gel. Lane 0: 10 bp ladder. Lanes 1-8: The samples are as described in entries 1-8 of the truth table. The gate used in this experiment is as shown in panel A, except that for historical reasons strand A rather than Aout was used; these strands differ only in the bulge loop sequence.

FIG. 20 shows a sequence translation, logic operations and signal restoration. For all fluorescence experiments, gates are mixed initially to a concentration of 250 nM per gate. DNA equivalents of the biological microRNAs are used throughout. Panel A shows an implicit OR gate. The two translator gates take two different microRNAs as inputs, but their output strands $S_{out}$ and $U_{out}$ have the same recognition regions and both bind to gate strand $D_m$ (which differs from strand D only in its toe-hold domain). Either of the two microRNAs together with $B_{in}$ and $C_{in}$ trigger the fluorescence signal. All inputs for a given fluorescence trace are added at the same time and at 300 nM. The output is triggered only if at least one of mir-15a or mir-10b is present together with Bin and Cin (blue, red, and green traces). If both mir-15a and mir-10b, or $B_{in}$, or $C_{in}$ are left out, the gate remains untriggered (black, cyan, and brown traces). Panel B shows a logical NOT gate. All inputs for a given fluorescence trace are added at the same time and at 300 nM. If let-7c is present, inverter strand K will preferentially hybridize to let-7c rather than triggering the translator (red trace). If no let-7c is present, inverter strand K will trigger the translator (blue trace). The gate strand let-7c3 contains a 3 nt extension that serves to reduce spurious triggering (see FIG. 22. Panel C shows thresholding. Strand Th2$_{in}$ is part of the thresholding unit and is added before the start of the experiment. In the experiment, a dye/quencher-labeled "read-out" gate is used to monitor the state of the threshold gate. On the right, the final fluorescence of the read-out is plotted against input concentration. The input-output relationship shows sigmoidal behavior.

FIG. 21 shows signal propagation through a complex chemical circuit combining AND, OR, sequence translation, input amplification and signal restoration. The circuit consists of a total of eleven gates and accepts six inputs. The input sequences are biological microRNAs but DNA equivalents of the biological microRNAs are used throughout. With the exception of the threshold gate which is at 100 nM (Th2$_{in}$ is at 150 nM), all gates are at 200 nM (1×) per gate. Unless otherwise specified, inputs were added at 250 nM (1.25×). Mir-143 was added at 50 nM (0.25×) and subsequently amplified by the input amplifier. The inset graphs show fluorescence traces of circuit operation with and without the signal restoration module (threshold plus amplifier). The traces for input conditions corresponding to a logical TRUE output (labeled "ON") are clearly distinguishable from the logical FALSE output (labeled "OFF"). The case where all inputs are present (blue trace), all cases where one input is missing (red, green, black, cyan, purple and yellow traces), were tested. In addition, withholding combinations of inputs constituting an OR clause (brown and orange traces) were tested. Assuming monotonicity, withholding additional inputs will not lead to a logical TRUE output. To determine the response of the circuit to a leaky OFF signal, input mir-124 was added at 50 nM (0.25×) while all other inputs were added normally (pink trace). Comparison of the response of the circuit with and without signal restoration illustrates that the signal restoration unit can significantly decrease the amount of spurious activation due to a leaky OFF signal.

Figure 22A:
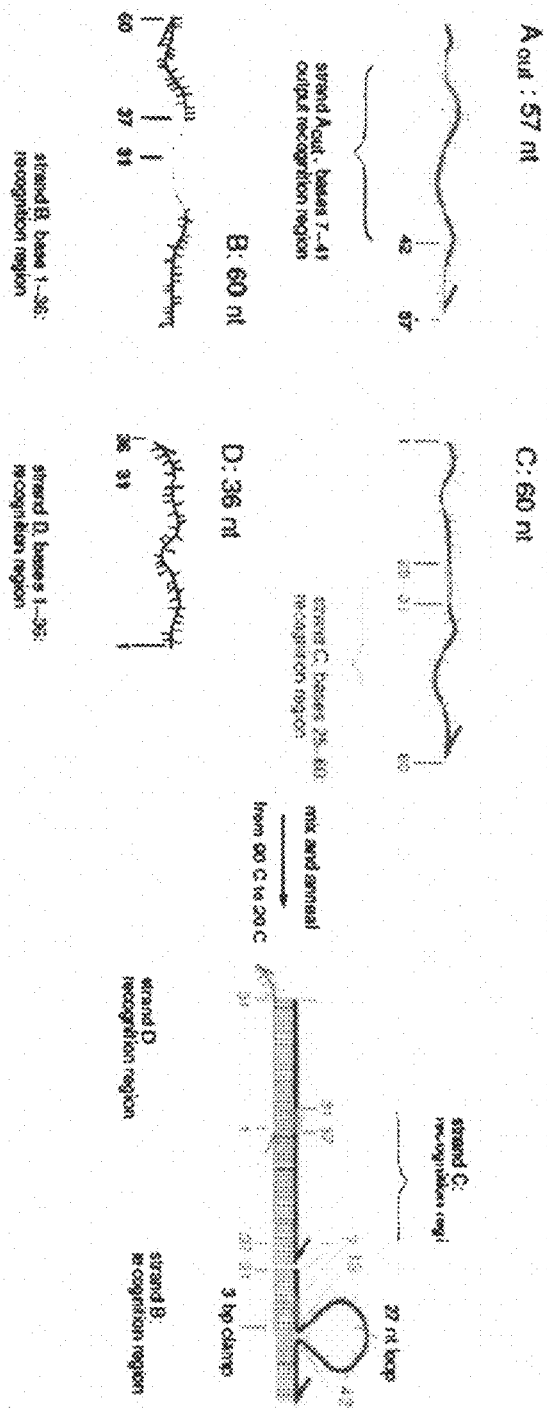
FIG. 22, panel A depicts exemplary gate design and assembly.
Figure 22B:
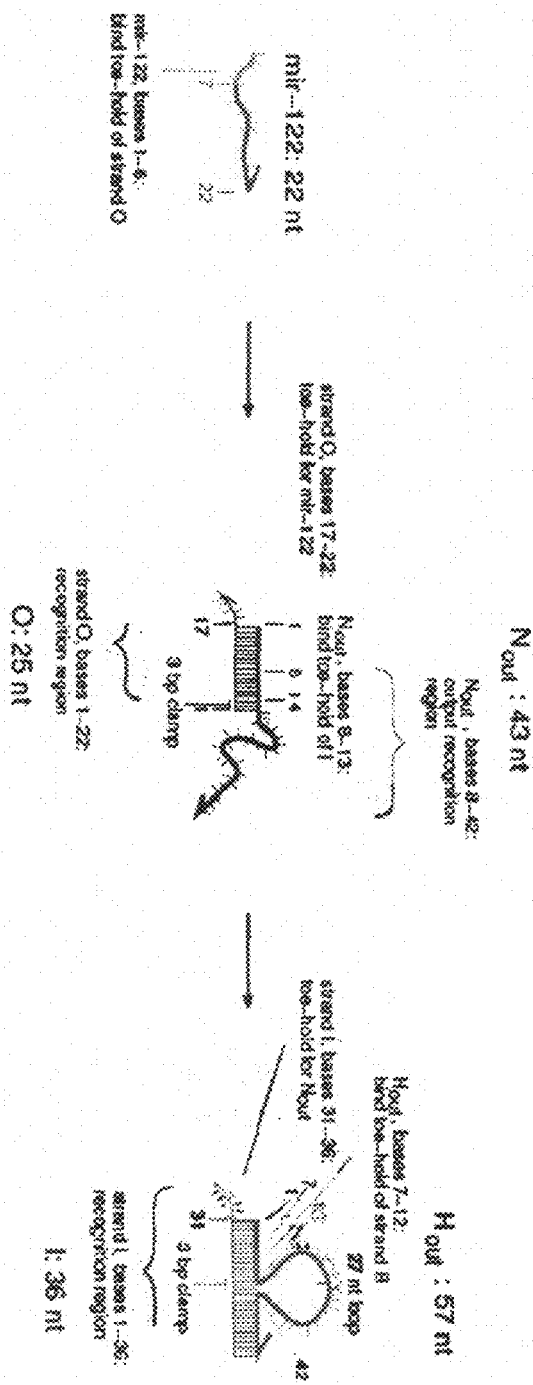

FIG. 22 shows an exemplary gate design. All exemplary toe-hold sequences and exemplary toe-hold binding sequences are indicated in color. Sequences of identical color bind to each other. Numbers refer to bases and the first base in every sub-sequence (i.e. region of different color) is indicated. In unbound strands the last base of the strand is also labeled explicitly. Panel A shows gate design and assembly. Constituent strands of a three input AND gate and the final assembled gate are shown. Recognition regions are indicated. If the output strand $A_{out}$ is bound there are three base pairs between the (double-stranded) toe-hold binding sequence (red) and the single-stranded loop. The toe-hold binding region was shifted inward to minimize interactions of a bound output strand with down-stream gates due to spontaneous fraying of the double helix at the nick. This choice implies that a total of nine nucleotides are common to the upstream input and the downstream recognition region. Panel B shows a two-stage translator cascade. The length of the recognition region of the first translator is imposed by the length of the microRNA. Only one end of output strand $N_{out}$ is bound to strand O. In order to better protect the toe-hold binding sequence, a three base clamp is introduced. Note that strand O is longer than the input strand mir-122 and that the three nucleotides constituting the clamp remain single stranded when input mir-122 is fully bound. These three bases on strand O in principle provide a toe-hold for the reverse reaction, i.e. $N_{out}$ binds to O and kicks off mir-122. The second translator in the cascade (gate HI) is designed analogously to the gate described in FIG. 22, panel A.

Figure 23:
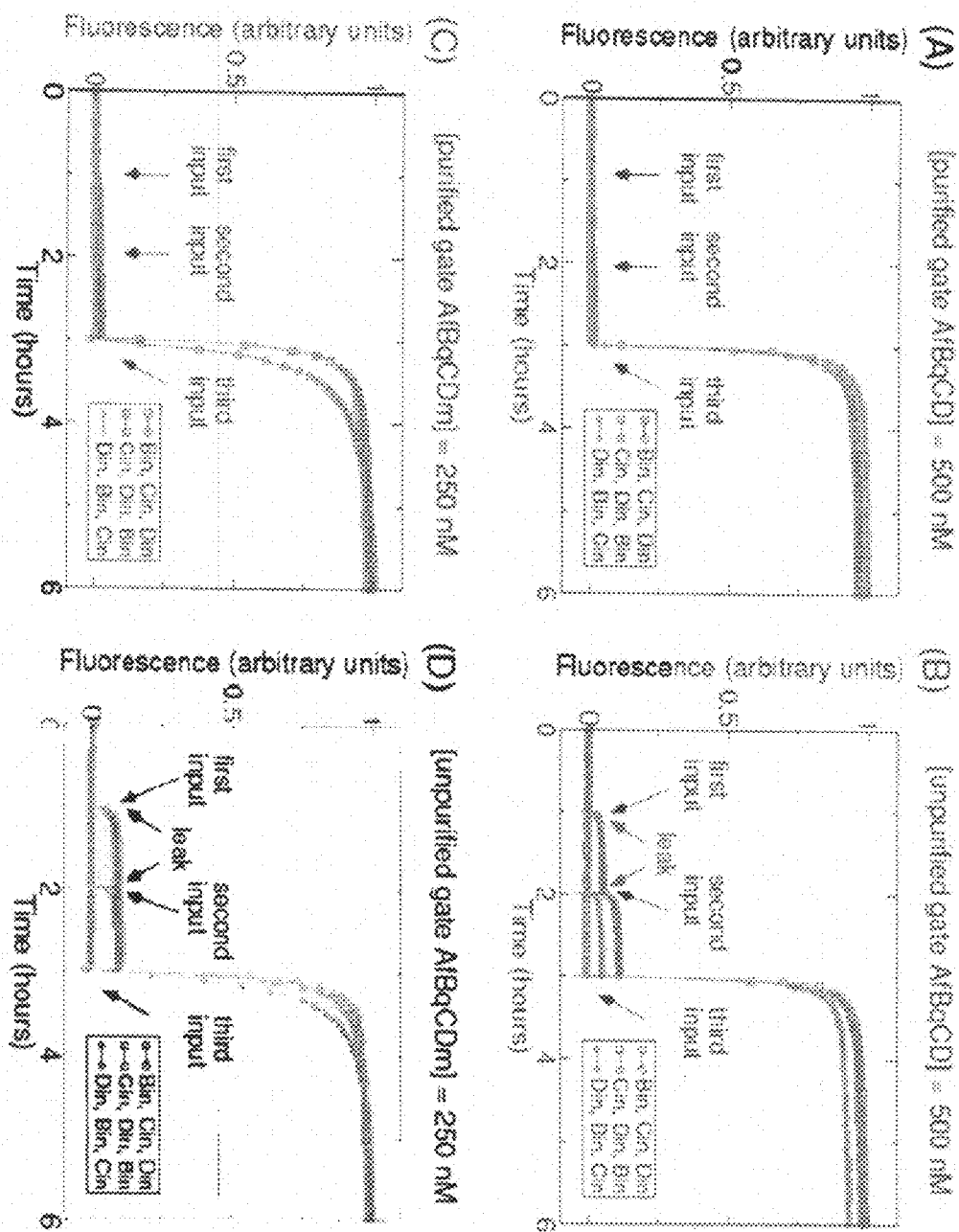
FIG. 23, panels A-B, depict a comparison of fluorescence in purified and unpurified gates for a three-input AND gate.

FIG. 23 shows three-input AND gate fluorescence data comparison of purified and unpurified gates. Panel A shows purified AND gate ABCD at 500 nM concentration (same data as shown in FIG. 19, panel D. Panel B shows unpurified AND gate ABCD at 500 nM concentration. The strands used for the gates in panels A and B came from the same DNA stocks. Panel C shows purified AND gate $ABCD_m$ at 250 nM concentration. Panel D shows unpurified AND gate $ABCD_m$ at 250 nM concentration. Note that the only difference between strands D and $D_m$ is the sequence of the six nucleotide toe-hold. The gates are otherwise identical. Comparison of Panel A) and B (or panel C and D) shows that purification decreases the amount of false positive signal. For the samples containing unpurified gates (see panel B and panel D) a spurious signal is observed even if only some subset of inputs is present.

FIG. 24 shows fluorescence data for the threshold circuit of FIG. 20, panel C. All three data sets (see panels A, B and C) are normalized to the maximal signal reached within the respective set of experiments. Panel A shows threshold gate and readout gate at 250 nM, $Th2_{in}$ at 300 nM and varying input concentrations. Panel B shows threshold and readout gate at 125 nM, $Th2_{in}$ at 150 nM and varying input concentrations. Panel C shows similar conditions as panel A but with gates from a different purification run. Panel D shows each data point corresponds to the final (normalized) fluorescence value reached in one kinetics experiment. Final fluorescence values are plotted against input concentration. Blue and red curve are the same as in FIG. 20, panel C. The blue curve is obtained from the data shown in panel B, the red curve is obtained from the data in panel A and the green curve form the data in panel C. Comparison of the red and green curves shows that thresholding behavior can be reproduced with gates from different purifications.

FIG. 25 shows signal amplification circuits. Panel A shows a signal amplifier. The amplifier gate is at 250 nM concentration. The sequences were changed relative to the original hybridization catalyst such that strand $Th_{out}$ can be used as an input. With the original sequences, reaction half-times in a single turnover situation at 250 nM were on the order of 5-10 minutes and in a multiple turnover situation a single catalyst strand (input) could catalyze the decay of up to 40 amplifier gates (there called "fuel complexes"). Here the reaction half-time is on the order of 20-30 minutes and a single strand turns over only about ten amplifier molecules. Panel B shows an amplifier based on feedback. Both gates are at 500 nM concentration. In these experiments, strand A (input to gate WY) was used to initiate the feedback loop. When the amplifier is used in the context of a circuit, strand $Th_{out}$ will serve as input. Note that $Th_{out}$ is an input to the dye-labeled gate $Q_{out}P_f$ and $Q_{out}P_f$ can thus be used by itself as a readout gate. For testing of the amplifier, strand A is a better choice since both gates need to be triggered before a signal increase is observed. Half-times in a single turnover situation (at 500 nM) are on the order of 5 min. The feedback system is less stable than the catalytic amplifier in the absence of input. Some spontaneous triggering can be clearly observed when gate WY is added to a solution containing $Q_{out}F_f$.

Figure 26:
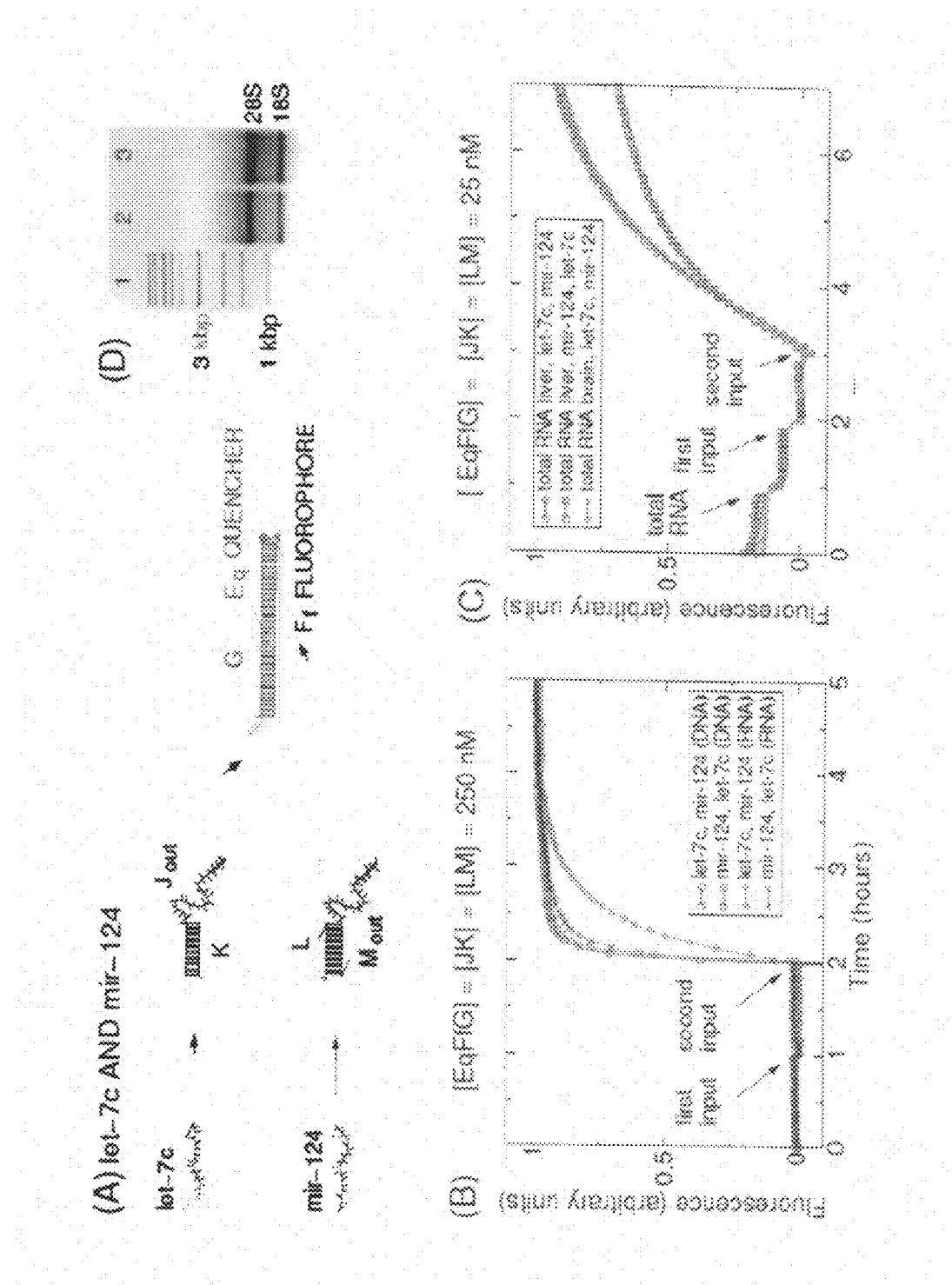
FIG. 26, panels A-D, depict logic with RNA inputs.
Figure 27:
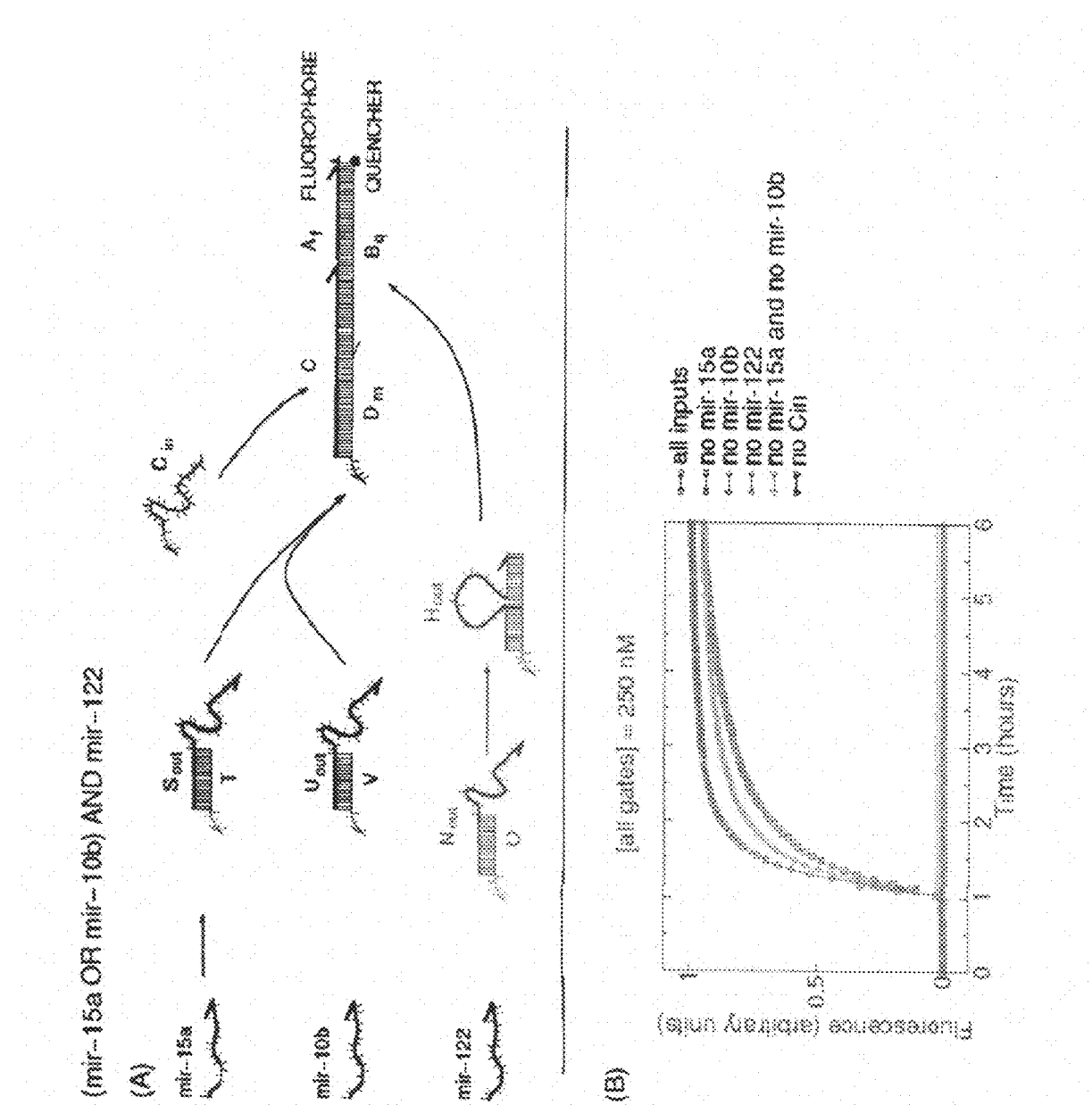
FIG. 27, panels A and B, depict implicit OR and full translator.

FIG. 26 shows a logic circuit with RNA inputs. Panel A shows a logic circuit for the calculation to the logical AND of two microRNA inputs. The circuit is very similar to the one shown in FIG. 20, panel B, for the calculation of mir-124 AND NOT let-7c. Panel B shows a comparison of reaction kinetics with DNA and RNA inputs. All gates are at 250 nM and inputs are at 300 nM concentration. Blue and red trace: DNA inputs. The order of input addition is interchanged between the two traces. In this way, all four cases of the truth table (i.e. no inputs, only mir-124, only let-7c, both inputs) can be tested in only two experiments. Green and black trace: RNA inputs. Panel C shows a gate operation in a total RNA background. All gates are at 25 nM, synthetic RNA inputs are at 50 nM. Total RNA is added first and then the two input strands are added in sequence. The order of input addition is interchanged between the red and the blue trace and two different total RNA samples are used. Blue and red trace: total RNA from mouse liver. Green trace: total RNA from mouse brain. Total RNA is at a concentration of 50 ug/ml. For comparison, a concentration of 50 nM for a single input strand species corresponds to about 0.5 ug/ml RNA. Total RNA samples mainly consist of ribosomal 18S and 28S RNA. The concentration of gates or added RNA inputs is several orders of magnitude higher than the concentration of any microRNA contained in the total RNA samples. The experiment demonstrates that the gates work reliably in a background of RNA with random sequences and at higher total concentration than both gates or inputs. Panel D shows a 1% non-denaturing agarose gel stained with ethidium bromide. Lane 1:1 kbp ladder (linear, double-stranded DNA); lane 2: mouse liver total RNA; lane 3: mouse brain total RNA. 18S and 28S ribosomal RNA bands are clearly visible. The gel serves as a verification that RNA samples were intact at the time when the fluorescence experiments of panel C were run.

FIG. 27 shows an implicit OR circuit and full translator. All gates are at 250 nM concentration and the inputs are at 300 nM. This circuit is an extended version of the implicit-OR circuit shown in FIG. 20, panel A. Instead of adding input strand $B_{in}$ directly as was done there, here mir-122 is used as an input and is translated into strand $H_{out}$. The recognition region of $H_{out}$ has the same sequence as $B_{in}$. Note that the sequence of input $H_{out}$ is completely unrelated to the sequence of mir-122. If a single translator was used instead of the full translator (i.e. a cascade of two translators) this would not be true. In fact, strand $N_{out}$ has six nucleotides in common with mir-122.

FIG. 28 shows a circuit with input amplifier. All gates at 250 nM, all inputs except mir-143 are at 300 nM (1.20×), while mir-143 is at 50 nM (0.20×). Note that mir-122 and mir-143 are coupled in an OR-clause. Only one of these two inputs thus is necessary for a logical TRUE output. In a situation where mir-122 is missing (and mir-143 is present) reaction kinetics are relatively slow since a substoichiometric amount of input needs to be catalytically amplified in order to fully trigger the fluorescently labeled three-input AND gate.

FIG. 29 shows a circuit with feedback-amplified output. All gates except threshold are at 200 nM, the threshold gate is at 75 nM concentration. Input mir-143 is at 50 nM (0.25×) while all other inputs are at 250 nM (1.25×) concentration. When all inputs are present (blue trace), all cases where exactly one input is missing (red, green, black, cyan, purple and yellow traces), were tested. In addition, we tested withholding combinations of inputs constituting an OR clause (brown and orange traces). Assuming monotonicity, withholding additional inputs will not lead to a logical TRUE output.

Applications for the gates and circuits provided herein include, but are not limited to the following.

1) In vitro computation: A crucial part of any sophisticated nanomachine is the control logic. Although modern lithography allows the creation of circuits operating at the nanoscale, very sophisticated and expensive equipment is required. Logic components fabricated out of DNA molecules suggest the possibility that large amounts of such components can be made easily through extremely inexpensive and high throughput methods of template duplication of DNA (e.g. PCR). Further, the easily achievable high density of these components in a single test tube allows for massive parallel processing, possibly useful for complex combinatorial problems.

Because DNA serves as the energy source, substrate (input and output) and device (gate), the present method of implementing logic circuits is a natural candidate for interfacing with biological systems. Nucleic acid circuits may eventually be used to detect the presence and type of dangerous biological activity. In addition, the circuits could be useful in the in vitro diagnosis of diseases from blood/tissue samples.

2) In situ detection of gene expression: The present logic components may be used for localizing gene expression in tissue sections. The current way of localizing gene expression in situ is using probe hybridization techniques such as in situ hybridization. The problem with existing methods is that they are only capable of using simple criteria for labeling. For example, coloring exactly those cells that possess a particular pattern of expression of a large number of genes requires a number of tissue sections proportional to the number of genes. The AND gates provided herein can be used to label according to a complex set of conditions (arbitrary Boolean logic expressions) without requiring processing multiple tissue slices.

Further, since the present gates use branch migration rather than hybridization to ensure sequence specificity, they may be more sequence specific than existing in situ techniques. Indeed, four way branch migration (as described above) is known to be sensitive to single base changes.

3) In vivo control of biological functions: Another application of enzyme-free biomolecular logic and computation is the eventual in vivo detection of disease. Disease markers such as mRNA, microRNA, and ssDNA (in the case of certain viruses) form the inputs to the logic circuits implemented by the methods described in this report. The output of the biomolecular logic may be the translation of an output protein, production of microRNAs or activation of an anti-sense RNA. The output may serve to offset the biochemical imbalance caused by the disease in a controlled manner, kill the affected cells, or signal the presence of disease in a manner that can be detected by external scans.

Because of the universality of mRNA and its involvement in almost every facet of cellular activity, it is possible that the method of enzyme-free biomolecular computation may be extended to detect and possibly remediate a wide variety of conditions.

The examples set forth above are provided to give those of ordinary skill in the art a complete disclosure and description of how to make and use the embodiments of the devices, systems and methods of the invention, and are not intended to limit the scope of what the inventors regard as their invention. Modifications of the above-described modes for carrying out the invention that are obvious to persons of skill in the art are intended to be within the scope of the following claims. All patents and publications mentioned in the specification are indicative of the levels of skill of those skilled in the art to which the invention pertains. All references cited in this disclosure are incorporated by reference to the same extent as if each reference had been incorporated by reference in its entirety individually.

A number of embodiments of the invention have been described. Nevertheless, it will be understood that various modifications may be made without departing from the spirit and scope of the invention. Accordingly, other embodiments are within the scope of the following claims.

What is claimed is:

1. A logic gate complex comprising:
   a) at least one output oligonucleotide comprising:
      i) a first region comprising at least one toehold binding domain that forms a duplex with a complementary nucleic acid sequence of a gate oligonucleotide;
      ii) a second region linked with the first region and comprising at least one single-stranded domain comprising an oligonucleotide that, upon release, functions as an input oligonucleotide sequence for a subsequent logic gate or as a signal sequence for detection of an operation, or a combination thereof;
      iii) a third region linked with the second region and comprising a nucleic acid sequence that forms a duplex with a complementary nucleic acid sequence of a gate oligonucleotide;
   b) at least one gate oligonucleotide comprising:
      i) a first region comprising a single-stranded toehold binding domain complementary to an input oligonucleotide sequence;
      ii) a second region comprising a nucleic acid sequence complementary to, and forming a duplex with, the first and third regions of the output oligonucleotide.

2. The logic gate of claim 1, wherein the output or input oligonucleotide is 10 to about 200 nucleotides in length.

3. The logic gate of claim 1, wherein the output or input oligonucleotide is 10 to about 100 nucleotides in length.

4. The logic gate of claim 1, wherein the output or input oligonucleotide is 10 to about 50 nucleotides in length.

5. The logic gate of claim 1, wherein the output oligonucleotide functions as an input oligonucleotide to a downstream gate.

6. The logic gate of claim 1, wherein the output oligonucleotide and input oligonucleotide comprise RNA or DNA.

7. The logic gate of claim 1, wherein the output oligonucleotide is detectably labeled.

8. The logic gate of claim 7, wherein the detectable label is a fluorescent label.

9. The logic gate of claim 7, wherein the detectable label comprises a material whose conductivity changes to indicate an output state.

10. The logic gate of claim 7, wherein the detectable label comprises a material whose magnetization changes to indicate the output state.

11. The logic gate of claim 1, wherein both the 5' and 3' ends of the output oligonucleotide are initially attached to the gate complex.

12. The logic gate of claim 1, wherein the gate is a logical AND gate.

13. The logic gate of claim 1, wherein the gate is a logical AND NOT gate.

14. The logic gate of claim 1, wherein the gate is a logical NOT gate.

15. The logic gate of claim 1, wherein the gate is a logical sensor gate, wherein an input is transduced into an output.

16. The logic gate of claim 1, wherein the input oligonucleotide is an oligonucleotide associated with a disease marker.

17. A plurality of logic gates of claim 1, wherein the output of one gate is the input of another gate.

18. The logic gate of claim 1, wherein the input oligonucleotide or output oligonucleotide comprises a peptide nucleic acid.

19. A method of performing a logical operation comprising:
   a) contacting the gate of claim 1 with a first input oligonucleotide that forms a duplex with a first toe-hold binding domain of a first gate oligonucleotide, wherein the first gate oligonucleotide is partially duplexed with a gate complex;
   b) displacing the gate oligonucleotide from the gate complex by branch migration, thereby exposing a second toe-hold binding domain of a second gate oligonucleotide duplexed with an output oligonucleotide;
   c) contacting the second toe-hold binding domain with a second input oligonucleotide;
   d) displacing the second gate oligonucleotide from the gate complex by branch migration, thereby releasing the output oligonucleotide,
   wherein release of the output oligonucleotide indicates that a logical operation has been performed.

20. The method of claim 19, wherein the output oligonucleotide functions as an input nucleotide sequence for a subsequent logical operation or as a signal sequence for detection of an operation, or a combination thereof.

21. The method of claim 20, wherein the output oligonucleotide is detectably labeled.

22. The method of claim 21, wherein the detectable label is a fluorescent label.

23. The method of claim 21, wherein the detectable label comprises a material whose conductivity changes to indicate an output state.

24. The method of claim 21, wherein the detectable label comprises a material whose magnetization changes to indicate the output state.

25. The method of claim 19, wherein the input oligonucleotide is an oligonucleotide associated with a disease marker.

26. The method of claim 19, wherein the operation is detection of a disease marker.

27. The method of claim 19, wherein the operation is transduction of an output oligonucleotide to at least one other gate.

28. The method of claim 27, wherein the different gate is a logical AND gate.

29. The method of claim 27, wherein the different gate is a logical AND NOT gate.

30. The method of claim 27, wherein the different gate is a NOT gate.

31. The method of claim 27, wherein the at least one other gate is a translator gate that can interconvert signals represented by different oligonucleotides.

32. The method of claim 27, wherein the different gate is a repeater gate.

33. The method of claim 19, wherein the gate is a logical sensor gate.

34. The method of claim 31, wherein the translator gate provides an output oligonucleotide to a subcircuit.

35. A circuit comprising a plurality of logic gates of claim 1.

36. The circuit of claim 35, wherein the circuit is a Boolean circuit.

37. The circuit of claim 35, wherein the circuit computes in multi-rail logic.

* * * * *

SEQUENCE LISTING

<160> NUMBER OF SEQ ID NOS: 64

<210> SEQ ID NO 1
<211> LENGTH: 36
<212> TYPE: DNA
<213> ORGANISM: Artificial sequence
<220> FEATURE:
<223> OTHER INFORMATION: Input strand sequence Bin

<400> SEQUENCE: 1
ttggaggtgt ttatagcgga cccctactga gttgtg                       36

<210> SEQ ID NO 2
<211> LENGTH: 36
<212> TYPE: DNA
<213> ORGANISM: Artificial sequence
<220> FEATURE:
<223> OTHER INFORMATION: Input strand sequence Cin

<400> SEQUENCE: 2
ctccaagagt gatatgccaa tacaaaccac gaagac                       36

<210> SEQ ID NO 3
<211> LENGTH: 36
<212> TYPE: DNA
<213> ORGANISM: Artificial sequence
<220> FEATURE:
<223> OTHER INFORMATION: Input strand sequence Din

<400> SEQUENCE: 3
cggtttcaca ttacttttgc tgccttacga gtcttc                       36

<210> SEQ ID NO 4
<211> LENGTH: 36
<212> TYPE: DNA
<213> ORGANISM: Artificial sequence
<220> FEATURE:
<223> OTHER INFORMATION: Input strand sequence Dm;in

<400> SEQUENCE: 4
tttgtgcaca ttacttttgc tgccttacga gtcttc                       36

<210> SEQ ID NO 5
<211> LENGTH: 30
<212> TYPE: DNA
<213> ORGANISM: Artificial sequence
<220> FEATURE:
<223> OTHER INFORMATION: Input strand sequence Din-no-toe

<400> SEQUENCE: 5
cacattactt ttgctgcctt acgagtcttc                              30

<210> SEQ ID NO 6
<211> LENGTH: 21
<212> TYPE: DNA
<213> ORGANISM: Artificial sequence
<220> FEATURE:
<223> OTHER INFORMATION: Input strand sequence let-7c

<400> SEQUENCE: 6
tgaggtagta ggttgtatgg t                                       21

<210> SEQ ID NO 7
<211> LENGTH: 18

```
<212> TYPE: DNA
<213> ORGANISM: Artificial sequence
<220> FEATURE:
<223> OTHER INFORMATION: Input strand sequence let-7c-no-toe

<400> SEQUENCE: 7
agtaggttgt atggttgt                                              18

<210> SEQ ID NO 8
<211> LENGTH: 20
<212> TYPE: DNA
<213> ORGANISM: Artificial sequence
<220> FEATURE:
<223> OTHER INFORMATION: Input strand sequence mir-124

<400> SEQUENCE: 8
taaggcacgc ggtgaatgcc                                            20

<210> SEQ ID NO 9
<211> LENGTH: 17
<212> TYPE: DNA
<213> ORGANISM: Artificial sequence
<220> FEATURE:
<223> OTHER INFORMATION: Input strand sequence mir-124-no-toe

<400> SEQUENCE: 9
gattaaggca cgcggtg                                               17

<210> SEQ ID NO 10
<211> LENGTH: 22
<212> TYPE: DNA
<213> ORGANISM: Artificial sequence
<220> FEATURE:
<223> OTHER INFORMATION: Input strand sequence mir-15a

<400> SEQUENCE: 10
tagcagcaca taatggtttg tg                                         22

<210> SEQ ID NO 11
<211> LENGTH: 19
<212> TYPE: DNA
<213> ORGANISM: Artificial sequence
<220> FEATURE:
<223> OTHER INFORMATION: Input strand sequence mir-15a-no-toe

<400> SEQUENCE: 11
cacataatgg tttgtgcac                                             19

<210> SEQ ID NO 12
<211> LENGTH: 22
<212> TYPE: DNA
<213> ORGANISM: Artificial sequence
<220> FEATURE:
<223> OTHER INFORMATION: Input strand sequence mir-10b

<400> SEQUENCE: 12
ccctgtagaa ccgaatttgt gt                                         22

<210> SEQ ID NO 13
<211> LENGTH: 18
<212> TYPE: DNA
<213> ORGANISM: Artificial sequence
<220> FEATURE:
<223> OTHER INFORMATION: Input strand sequence mir-10b-no-toe

<400> SEQUENCE: 13
```
agaaccgaat tgtgcac                                             18

<210> SEQ ID NO 14
<211> LENGTH: 22
<212> TYPE: DNA
<213> ORGANISM: Artificial sequence
<220> FEATURE:
<223> OTHER INFORMATION: Input strand sequence mir-122

<400> SEQUENCE: 14
tggagtgtga caatggtgtt tg                                       22

<210> SEQ ID NO 15
<211> LENGTH: 19
<212> TYPE: DNA
<213> ORGANISM: Artificial sequence
<220> FEATURE:
<223> OTHER INFORMATION: Input strand sequence mir-122-no-toe

<400> SEQUENCE: 15
gtgacaatgg tgtttggat                                           19

<210> SEQ ID NO 16
<211> LENGTH: 22
<212> TYPE: DNA
<213> ORGANISM: Artificial sequence
<220> FEATURE:
<223> OTHER INFORMATION: Input strand sequence mir-143

<400> SEQUENCE: 16
tgagatgaag cactgtagct ca                                       22

<210> SEQ ID NO 17
<211> LENGTH: 30
<212> TYPE: DNA
<213> ORGANISM: Artificial sequence
<220> FEATURE:
<223> OTHER INFORMATION: Input strand sequence Gin-no-toe

<400> SEQUENCE: 17
tgtttatgtg ttccctgatc tttagcctta                               30

<210> SEQ ID NO 18
<211> LENGTH: 30
<212> TYPE: DNA
<213> ORGANISM: Artificial sequence
<220> FEATURE:
<223> OTHER INFORMATION: Input strand sequence Iin-no-toe

<400> SEQUENCE: 18
gatgaattgg aggtgggata ttattactga                               30

<210> SEQ ID NO 19
<211> LENGTH: 36
<212> TYPE: DNA
<213> ORGANISM: Artificial sequence
<220> FEATURE:
<223> OTHER INFORMATION: Input strand sequence Th2in

<400> SEQUENCE: 19
cgctatctga ctgactgtta ccgatttgtt tcattc                        36

<210> SEQ ID NO 20
<211> LENGTH: 57
<212> TYPE: DNA
<213> ORGANISM: Artificial sequence

```
<220> FEATURE:
<223> OTHER INFORMATION: strand A

<400> SEQUENCE: 20
gtgtttatag cggactgacg gtttcactac cctgttgttc taccctactg agttgtg        57

<210> SEQ ID NO 21
<211> LENGTH: 57
<212> TYPE: DNA
<213> ORGANISM: Artificial sequence
<220> FEATURE:
<223> OTHER INFORMATION: strand Aout

<400> SEQUENCE: 21
gtgtttatag cggacttact agatttatac cctgttgaat gaccctactg agttgtg        57

<210> SEQ ID NO 22
<211> LENGTH: 30
<212> TYPE: DNA
<213> ORGANISM: Artificial sequence
<220> FEATURE:
<223> OTHER INFORMATION: strand Af

<400> SEQUENCE: 22
gtgtttatag cggaccccta ctgagttgtg                                       30

<210> SEQ ID NO 23
<211> LENGTH: 60
<212> TYPE: DNA
<213> ORGANISM: Artificial sequence
<220> FEATURE:
<223> OTHER INFORMATION: strand B

<400> SEQUENCE: 23
cacaactcag taggggtccg ctataaacac ctccaagagt gatatgccaa tacaaaccac      60

<210> SEQ ID NO 24
<211> LENGTH: 60
<212> TYPE: DNA
<213> ORGANISM: Artificial sequence
<220> FEATURE:
<223> OTHER INFORMATION: strand Bq

<400> SEQUENCE: 24
cacaactcag taggggtccg ctataaacac ctccaagagt gatatgccaa tacaaaccac      60

<210> SEQ ID NO 25
<211> LENGTH: 60
<212> TYPE: DNA
<213> ORGANISM: Artificial sequence
<220> FEATURE:
<223> OTHER INFORMATION: strand C

<400> SEQUENCE: 25
cacattactt tgctgccttt acgagtcttc gtggtttgta ttggcatatc actcttggag      60

<210> SEQ ID NO 26
<211> LENGTH: 36
<212> TYPE: DNA
<213> ORGANISM: Artificial sequence
<220> FEATURE:
<223> OTHER INFORMATION: strand D

<400> SEQUENCE: 26
gaagactcgt aaggcagcaa aagtaatgtg aaaccg                                36
```

```
<210> SEQ ID NO 27
<211> LENGTH: 36
<212> TYPE: DNA
<213> ORGANISM: Artificial sequence
<220> FEATURE:
<223> OTHER INFORMATION: strand sequence Dm

<400> SEQUENCE: 27
gaagactcgt aaggcagcaa aagtaatgtg cacaaa                          36

<210> SEQ ID NO 28
<211> LENGTH: 57
<212> TYPE: DNA
<213> ORGANISM: Artificial sequence
<220> FEATURE:
<223> OTHER INFORMATION: strand sequence Eout

<400> SEQUENCE: 28
gttagatgtt agtttctcca agagtgatat gccaatacaa accacgaaga caatgat   57

<210> SEQ ID NO 29
<211> LENGTH: 30
<212> TYPE: DNA
<213> ORGANISM: Artificial sequence
<220> FEATURE:
<223> OTHER INFORMATION: strand sequence Eq

<400> SEQUENCE: 29
gttagatgtt agtttcacga agacaatgat                                 30

<210> SEQ ID NO 30
<211> LENGTH: 60
<212> TYPE: DNA
<213> ORGANISM: Artificial sequence
<220> FEATURE:
<223> OTHER INFORMATION: strand sequence F

<400> SEQUENCE: 30
tgtttatgtg ttccctgatc tttagcctta atcattgtct tcgtgaaact aacatctaac 60

<210> SEQ ID NO 31
<211> LENGTH: 60
<212> TYPE: DNA
<213> ORGANISM: Artificial sequence
<220> FEATURE:
<223> OTHER INFORMATION: strand sequence Ff

<400> SEQUENCE: 31
tgtttatgtg ttccctgatc tttagcctta atcattgtct tcgtgaaact aacatctaac 60

<210> SEQ ID NO 32
<211> LENGTH: 36
<212> TYPE: DNA
<213> ORGANISM: Artificial sequence
<220> FEATURE:
<223> OTHER INFORMATION: strand sequence G

<400> SEQUENCE: 32
taaggctaaa gatcagggaa cacataaaca accata                          36

<210> SEQ ID NO 33
<211> LENGTH: 36
<212> TYPE: DNA
<213> ORGANISM: Artificial sequence
<220> FEATURE:
<223> OTHER INFORMATION: strand sequence Gnot
```

<400> SEQUENCE: 33
taaggctaaa gatcagggaa cacataaaca tgaggt        36

<210> SEQ ID NO 34
<211> LENGTH: 57
<212> TYPE: DNA
<213> ORGANISM: Artificial sequence
<220> FEATURE:
<223> OTHER INFORMATION: strand sequence Hout

<400> SEQUENCE: 34
gatgaattgg aggtgtttat agcggacccc tactgagttg tgggatatta ttactga        57

<210> SEQ ID NO 35
<211> LENGTH: 36
<212> TYPE: DNA
<213> ORGANISM: Artificial sequence
<220> FEATURE:
<223> OTHER INFORMATION: strand sequence I

<400> SEQUENCE: 35
tcagtaataa tatcccacct ccaattcatc caaaca        36

<210> SEQ ID NO 36
<211> LENGTH: 45
<212> TYPE: DNA
<213> ORGANISM: Artificial sequence
<220> FEATURE:
<223> OTHER INFORMATION: strand sequence Jout

<400> SEQUENCE: 36
agtaggttgt atggttgttt atgtgttccc tgatctttag cctta        45

<210> SEQ ID NO 37
<211> LENGTH: 45
<212> TYPE: DNA
<213> ORGANISM: Artificial sequence
<220> FEATURE:
<223> OTHER INFORMATION: strand sequence Jout;not

<400> SEQUENCE: 37
caacctacta cctcatgttt atgtgttccc tgatctttag cctta        45

<210> SEQ ID NO 38
<211> LENGTH: 24
<212> TYPE: DNA
<213> ORGANISM: Artificial sequence
<220> FEATURE:
<223> OTHER INFORMATION: strand sequence K

<400> SEQUENCE: 38
acaaccatac aacctactac ctca        24

<210> SEQ ID NO 39
<211> LENGTH: 24
<212> TYPE: DNA
<213> ORGANISM: Artificial sequence
<220> FEATURE:
<223> OTHER INFORMATION: strand sequence let-7c3

<400> SEQUENCE: 39
acatgaggta gtaggttgta tggt        24

<210> SEQ ID NO 40

```
<211> LENGTH: 23
<212> TYPE: DNA
<213> ORGANISM: Artificial sequence
<220> FEATURE:
<223> OTHER INFORMATION: strand sequence L

<400> SEQUENCE: 40
ggcattcacc gcgtgcctta atc                                              23

<210> SEQ ID NO 41
<211> LENGTH: 44
<212> TYPE: DNA
<213> ORGANISM: Artificial sequence
<220> FEATURE:
<223> OTHER INFORMATION: strand sequence Mout

<400> SEQUENCE: 41
gttagatgtt agtttcacga agacaatgat taaggcacgc ggtg                       44

<210> SEQ ID NO 42
<211> LENGTH: 46
<212> TYPE: DNA
<213> ORGANISM: Artificial sequence
<220> FEATURE:
<223> OTHER INFORMATION: strand sequence Nout

<400> SEQUENCE: 42
gtgacaatgg tgtttggatg aattggaggt gggatattat tactga                     46

<210> SEQ ID NO 43
<211> LENGTH: 25
<212> TYPE: DNA
<213> ORGANISM: Artificial sequence
<220> FEATURE:
<223> OTHER INFORMATION: strand sequence O

<400> SEQUENCE: 43
atccaaacac cattgtcaca ctcca                                            25

<210> SEQ ID NO 44
<211> LENGTH: 36
<212> TYPE: DNA
<213> ORGANISM: Artificial sequence
<220> FEATURE:
<223> OTHER INFORMATION: strand sequence Pf

<400> SEQUENCE: 44
aacagggtaa ctcaggaaca ggtccgctat gtcagg                                36

<210> SEQ ID NO 45
<211> LENGTH: 57
<212> TYPE: DNA
<213> ORGANISM: Artificial sequence
<220> FEATURE:
<223> OTHER INFORMATION: strand sequence Qout

<400> SEQUENCE: 45
cctgacatag cggactgacg gtttcactac cctgttgttc tactgttcct gagttac         57

<210> SEQ ID NO 46
<211> LENGTH: 52
<212> TYPE: DNA
<213> ORGANISM: Artificial sequence
<220> FEATURE:
<223> OTHER INFORMATION: strand sequence R1

<400> SEQUENCE: 46
```
cacctccaat tcatcaatga gggtgacttc tgagctacag tgcttcatct ca        52

<210> SEQ ID NO 47
<211> LENGTH: 71
<212> TYPE: DNA
<213> ORGANISM: Artificial sequence
<220> FEATURE:
<223> OTHER INFORMATION: strand sequence R2

<400> SEQUENCE: 47
gaagcactgt agctcacaca cagtagatca gaattggcac gttcgctcgc taggttgaag    60
tcaccctcat t        71

<210> SEQ ID NO 48
<211> LENGTH: 75
<212> TYPE: DNA
<213> ORGANISM: Artificial sequence
<220> FEATURE:
<223> OTHER INFORMATION: strand sequence R3

<400> SEQUENCE: 48
atcaatgagg gtgacttcaa cctagcgagc gaacgtgcca attctgatct actgtgtgtg    60
agctacagtg cttca        75

<210> SEQ ID NO 49
<211> LENGTH: 44
<212> TYPE: DNA
<213> ORGANISM: Artificial sequence
<220> FEATURE:
<223> OTHER INFORMATION: strand sequence R4

<400> SEQUENCE: 49
tgaagcactg tagctcagaa gtcaccctca ttgatgaatt ggag        44

<210> SEQ ID NO 50
<211> LENGTH: 42
<212> TYPE: DNA
<213> ORGANISM: Artificial sequence
<220> FEATURE:
<223> OTHER INFORMATION: Rout

<400> SEQUENCE: 50
gatgaattgg aggtgtttat agcggacccc tactgagttg tg        42

<210> SEQ ID NO 51
<211> LENGTH: 46
<212> TYPE: DNA
<213> ORGANISM: Artificial sequence
<220> FEATURE:
<223> OTHER INFORMATION: strand sequence Sout

<400> SEQUENCE: 51
cacataatgg tttgtgcaca ttacttttgc tgccttacga gtcttc        46

<210> SEQ ID NO 52
<211> LENGTH: 25
<212> TYPE: DNA
<213> ORGANISM: Artificial sequence
<220> FEATURE:
<223> OTHER INFORMATION: strand sequence T

<400> SEQUENCE: 52
gtgcacaaac cattatgtgc tgcta        25

<210> SEQ ID NO 53
<211> LENGTH: 45
<212> TYPE: DNA
<213> ORGANISM: Artificial sequence
<220> FEATURE:
<223> OTHER INFORMATION: strand sequence Uout

<400> SEQUENCE: 53
agaaccgaat tgtgcacat tactttttgct gccttacgag tcttc        45

<210> SEQ ID NO 54
<211> LENGTH: 24
<212> TYPE: DNA
<213> ORGANISM: Artificial sequence
<220> FEATURE:
<223> OTHER INFORMATION: strand sequence V

<400> SEQUENCE: 54
gtgcacaaat tcggttctac aggg        24

<210> SEQ ID NO 55
<211> LENGTH: 57
<212> TYPE: DNA
<213> ORGANISM: Artificial sequence
<220> FEATURE:
<223> OTHER INFORMATION: strand sequence Wout

<400> SEQUENCE: 55
gactgacggt tcaccctga catagcggac ctgttcctga gttaccctgt tgttcta        57

<210> SEQ ID NO 56
<211> LENGTH: 36
<212> TYPE: DNA
<213> ORGANISM: Artificial sequence
<220> FEATURE:
<223> OTHER INFORMATION: strand sequence Y

<400> SEQUENCE: 56
tagaacaaca gggtagtgaa accgtcagtc cgctat        36

<210> SEQ ID NO 57
<211> LENGTH: 57
<212> TYPE: DNA
<213> ORGANISM: Artificial sequence
<220> FEATURE:
<223> OTHER INFORMATION: strand sequence Thout

<400> SEQUENCE: 57
gacttactag atttacctga catagcggac ctgttcctga gttaccctgt tgaatga        57

<210> SEQ ID NO 58
<211> LENGTH: 60
<212> TYPE: DNA
<213> ORGANISM: Artificial sequence
<220> FEATURE:
<223> OTHER INFORMATION: strand sequence Th1

<400> SEQUENCE: 58
tcattcaaca gggtataaat ctagtaagtc cgctatctga ctgactgtta ccgatttgtt        60

<210> SEQ ID NO 59
<211> LENGTH: 60
<212> TYPE: DNA
<213> ORGANISM: Artificial sequence
<220> FEATURE:
<223> OTHER INFORMATION: strand sequence Th2

<400> SEQUENCE: 59
gacttactag atttataccc tgttgaatga aacaaatcgg taacagtcag tcagatagcg    60

<210> SEQ ID NO 60
<211> LENGTH: 36
<212> TYPE: DNA
<213> ORGANISM: Artificial sequence
<220> FEATURE:
<223> OTHER INFORMATION: strand sequence Th1short

<400> SEQUENCE: 60
tcattcaaca gggtataaat ctagtaagtc cgctat    36

<210> SEQ ID NO 61
<211> LENGTH: 76
<212> TYPE: DNA
<213> ORGANISM: Artificial sequence
<220> FEATURE:
<223> OTHER INFORMATION: strand sequence CA2

<400> SEQUENCE: 61
aacagggtaa ctcaggaaca gcacacagta gatcagaatt ggcacgttcg ctcgctaggt    60
tgaagtcacc ctcatt    76

<210> SEQ ID NO 62
<211> LENGTH: 70
<212> TYPE: DNA
<213> ORGANISM: Artificial sequence
<220> FEATURE:
<223> OTHER INFORMATION: strand sequence CA3

<400> SEQUENCE: 62
aatgagggtg acttcaacct agcgagcgaa cgtgccaatt ctgatctact gtgtgctgtt    60
cctgagttac    70

<210> SEQ ID NO 63
<211> LENGTH: 30
<212> TYPE: DNA
<213> ORGANISM: Artificial sequence
<220> FEATURE:
<223> OTHER INFORMATION: strand sequence CA1

<400> SEQUENCE: 63
aatgagggtg acttcctgtt cctgagttac    30

<210> SEQ ID NO 64
<211> LENGTH: 30
<212> TYPE: DNA
<213> ORGANISM: Artificial sequence
<220> FEATURE:
<223> OTHER INFORMATION: strand sequence CA4

<400> SEQUENCE: 64
gtaactcagg aacaggaagt caccctcatt    30